United States Patent
Vankan et al.

(10) Patent No.: US 12,419,886 B2
(45) Date of Patent: *Sep. 23, 2025

(54) PARENTERAL FORMULATIONS AND USES THEREOF

(71) Applicant: Eustralis Pharmaceuticals Limited, Melbourne (AU)

(72) Inventors: Pierre Vankan, Melbourne (AU); Andreea Sasarman, Melbourne (AU); Grasiela Bourscheit Willmbrink, Melbourne (AU)

(73) Assignee: EUSTRALIS PHARMACEUTICALS LIMITED, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,979

(22) Filed: Sep. 26, 2023

(65) Prior Publication Data

US 2024/0091221 A1 Mar. 21, 2024

Related U.S. Application Data

(63) Continuation of application No. 16/966,286, filed as application No. PCT/AU2019/050075 on Feb. 1, 2019, now Pat. No. 11,801,244.

(30) Foreign Application Priority Data

Feb. 2, 2018 (AU) ................................ 2018900325

(51) Int. Cl.
*A61K 31/496* (2006.01)
*A61K 47/10* (2017.01)

(52) U.S. Cl.
CPC ............ *A61K 31/496* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 11,801,244 B2 | 10/2023 | Vankan et al. | |
| 2003/0004157 A1* | 1/2003 | Buser | A61P 13/08 |
| | | | 514/346 |
| 2006/0035903 A1* | 2/2006 | Mohr | A61K 47/12 |
| | | | 514/251 |
| 2016/0136160 A1* | 5/2016 | Vink | A61P 25/00 |
| | | | 514/253.13 |
| 2017/0283463 A1* | 10/2017 | Miller | A61P 31/04 |
| 2020/0368166 A1 | 11/2020 | Vankan et al. | |
| 2020/0368226 A1 | 11/2020 | Vankan et al. | |
| 2022/0073467 A1 | 3/2022 | Liakatos | |
| 2023/0124548 A1 | 4/2023 | Vankan et al. | |

FOREIGN PATENT DOCUMENTS

| | | |
|---|---|---|
| CN | 1523988 A | 8/2004 |
| CN | 101795690 A | 8/2010 |
| CN | 105358153 A | 2/2016 |
| JP | 2016523262 A | 8/2016 |
| WO | 03006016 A2 | 1/2003 |
| WO | 2003006016 A3 | 7/2003 |
| WO | 2009009829 A1 | 1/2009 |
| WO | 2015000033 A1 | 1/2015 |
| WO | 2019148246 A1 | 8/2019 |
| WO | 2019148247 A1 | 8/2019 |

OTHER PUBLICATIONS

Strickley et al (Pharmaceutical Research, 21(2), 2004). (Year: 2004).*
International Preliminary Report on Patentability for PCT/AU2019/050075, issued Aug. 4, 2020, and filed on Feb. 1, 2019, 5 pages.
International Search Report and Written Opinion, mailed Feb. 26, 2019, for PCT/AU2019/050075, filed Feb. 1, 2019, 9 pages.
Med India et al. (1997). "Routes of Drug Administration: Introduction on Routes of Drug Administration," 15 pages, retrieved on https://www.medindia.net/patientinfo/routes-of-drug-administration-print.htm.
Shaikh, A.C. et al. (Mar. 2022). "Review-Formulation Development Studies," International Journal of Creative Research Thoughts 10(3):D144-154.
University of Missouri—St. Louis (2010.) "Chapter 8 Solutions," USML, 28 pages, as retrieved on https://www.umsl.edu/~chickosj/56/temp8.pdf.
Declaration Under 37 C.F.R. 1.132 of Dr. Pierre Vankan dated Sep. 4, 2022, filed in U.S. Appl. No. 16/966,286, 17 pages.

* cited by examiner

*Primary Examiner* — Celeste A Roney
(74) *Attorney, Agent, or Firm* — MORRISON & FOERSTER LLP

(57) ABSTRACT

This invention relates generally to therapeutic parenteral formulations comprising particular substituted pyridine based compounds, their manufacture, and methods and uses of said formulations in treating elevated intracranial pressure for indications such as, but not limited to, traumatic brain injury and stroke.

8 Claims, No Drawings

PARENTERAL FORMULATIONS AND USES THEREOF

CROSS REFERENCE TO RELATED APPLICATIONS

This application is a continuation of U.S. application Ser. No. 16/966,286, filed internationally on Feb. 1, 2019, which is a national phase entry of International Application No. PCT/AU2019/050075, filed Feb. 1, 2019. which claims priority to Australian Patent Application No. AU 2018900325, filed Feb. 2, 2018, the disclosures of which are incorporated herein by reference in their entireties.

FIELD

This invention relates generally to therapeutic parenteral formulations comprising particular substituted pyridine based compounds, their manufacture, and methods and uses of said formulations in treating substance P mediated pathways in the brain such as elevated intracranial pressure or the modification of expression of (hyper)-phosphorylated tau protein ($\tau$) in the brain for indications such as, but not limited to concussion, post-concussive (or post-concussion) syndrome (PCS), chronic traumatic encephalopathy (CTE), traumatic brain injury (TBI) and stroke.

BACKGROUND

Traumatic brain injury (TBI), also known as intracranial injury, occurs when an external force injures the brain. TBI can be classified based on severity, mechanism (closed or penetrating head injury), or other features (e.g., occurring in a specific location or over a widespread area). TBI can result in physical, cognitive, social, emotional, and behavioural symptoms, and outcome can range from complete recovery to permanent disability or death.

Brain trauma occurs as a consequence of a sudden acceleration or deceleration within the cranium or by a complex combination of both movement and sudden impact. In addition to the damage caused at the moment of injury, a variety of events in the minutes to days following the injury may result in secondary injury, These processes include alterations in cerebral blood flow and the pressure within the skull.

The most common causes of TBI include violence, transportation accidents, construction, and sports. Motor bikes are major causes, increasing in significance in developing countries as other causes reduce. It is estimated that between 1.6 and 3.8 million traumatic brain injuries each year are a result of sports and recreation activities in the US, In children aged two to four, falls are the most common cause of TBI, while in older children traffic accidents compete with falls for this position. TBI is the third most common injury to result from child abuse. Abuse causes 19% of cases of paediatric brain trauma, and the death rate is higher among these cases.

There is a lack of effective medication that can lower elevated intracranial pressure (ICP) in TBI or stroke, neither is there any medication that can prevent the over-expression of hyper-phosphorylated tau protein which has been linked to bad clinical outcome in indications such as TBI but also Alzheimer's disease. Accordingly, there exists a need for a medication that can cure or ameliorate elevated ICP in TBI or stroke or prevent over-expression of hyper-phosphorylated tau protein.

The issue of the lack of effective medication is further compounded by the fact that patients with TBI are likely to be unconscious or may have difficulties swallowing. Accordingly, there is a limitation on how the medication may be administered.

Even while an active pharmaceutical ingredient (API) is identified, there are still many obstacles to overcome in formulating a drug. In formulating a drug suitable for human administration, the skilled person would be aware that the formulation art is not predictable. Various factors need to be carefully investigated and tuned to at least maintain (if not enhance) the pharmacokinetic properties of the API, and/or impart stability to the drug such that it can have an acceptable shelf-life. In this sense, the physical characteristic of the API, the mode of delivery, the flow properties of the composition, the excipient compatibility, the uniformity in production and the release profile needs to be carefully studied and investigated.

If not properly formulated, the API may not efficiently provide bioavailability to a patient. For example, while calcium salts can be utilized as fillers, it was found that they also interfere with the absorption of tetracycline (an example of an API) from the gastrointestinal tract, This one example emphasizes that components added in formulations may not always be inert, as one may perceive, and can interact with the API.

Further, the addition of diluents into a formulation may also alter the physical-chemical properties of the formulation which may render the product unstable and may cause problems in manufacturing. This is further compounded by the need for Good Manufacturing Practice (GMP) standards, as certain compliance of each ingredient with existing standards and regulations must be met in a pharmaceutical formulation for use as a drug.

The present invention seeks to overcome or ameliorate at least one of the shortcomings of the art in respect to the formulation of specific compounds.

SUMMARY OF THE INVENTION

The present invention provides therapeutic parenteral pharmaceutical formulations that comprises an effective amount of a particular substituted pyridine based compounds and other excipients, The parenteral formulation advantageously allows administration of the API to a subject in need thereof when the subject is unconscious or unable to swallow, for instance, a subject in need thereof by providing instant relief of substance P mediated processes such as over-expression of hyper-phosphorylated tau protein or elevated intracranial pressure (ICP) and accordingly immediately alleviate the condition and/or symptom of indications as such, but not limited to PCS, CTE, TBI and stroke. The formulations described herein are characterised at least by good API solubility when in the reconstituted form. The formulation is also characterised by good stability.

In a first aspect, the present invention provides a reconstitutable, parenteral, pharmaceutical composition comprising:
(i) a compound of Formula (I) or a pharmaceutically acceptable salt, solvate or prodrug thereof:

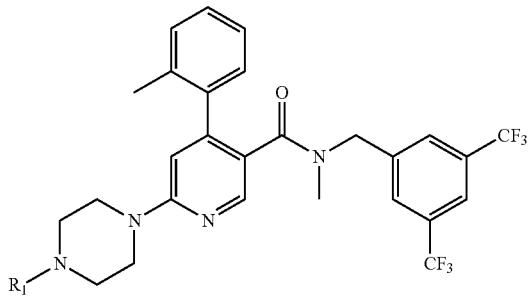

Formula (I)

wherein $R_1$ is H or $C_{1-4}$ alkyl; and
(ii) at least one solubiliser selected from the group comprising of a glycerol, glycerin, dimethylacetamide, N-methyl-2-pyrrolidone, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), polysorbate 80 (Tween 80), castor oil, cottonseed oil, triglyceride, sesame oil, soybean oil, or safflower oil, wherein the at least one solubiliser is present in the composition in an amount of about 10% to about 99.8% wt/wt based on the total weight of the composition.

In an embodiment, the compound of Formula (I) or a pharmaceutically acceptable salt, solvate or prodrug thereof is present in the composition in an amount of about 0.2% to about 1.8% wt/wt based on the total weight of the composition.

In another embodiment, the wt/wt ratio of compound of Formula (I) or a pharmaceutically acceptable salt, solvate or prodrug thereof to solubiliser is about 1:40 to about 1:250, In another embodiment, the reconstitutable, parenteral, pharmaceutical composition is a reconstitutable, intravenous, pharmaceutical composition, and the solubiliser is propylene glycol.

In a second aspect, the present invention provides a parenteral, pharmaceutical composition comprising:
(i) a compound of Formula (I) or a pharmaceutically acceptable salt, solvate or prodrug thereof:

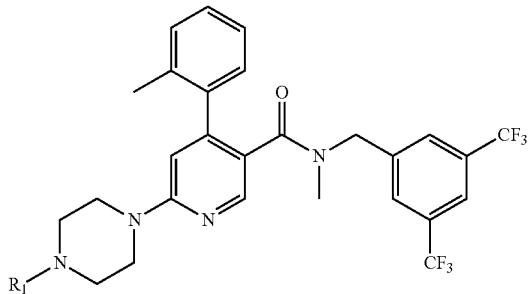

Formula (I)

wherein $R_1$ is H or $C_{1-4}$ alkyl; and
(ii) at least one solubiliser selected from the group comprising of a glycerol, glycerin, dimethylacetamide, N-methyl-2-pyrrolidone, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), polysorbate 80 (Tween 80), castor oil, cottonseed oil, triglyceride, sesame oil, soybean oil, or safflower oil; and
(iii) an infusion fluid selected from the group comprising of water, saline, potassium solution, glucose solution, glucose saline, dextrose solution, dextrose saline, balanced crystalloid solution, Hartmann's solution, Ringer's solution, lactated Ringer's solution, acetated Ringer's solution, Normosol-R, Normosol-M, Plasmalyte, plasma, human albumin, hydroxyethyl starch, dextran, whole blood, oxyglobin or a combination thereof.

In an embodiment, and with reference to the parenteral, pharmaceutical composition, the composition has an osmolality of about 200 mOsm/kg to about 650 mOsm/kg.

In an embodiment, the wt/wt ratio of the at least one solubiliser to the infusion fluid is about 1:10 to about 1:2000.

In another embodiment, the infusion fluid is a glucose solution of 5%.

In a third aspect, the present invention provides a method fur treating elevated intracranial pressure in a subject in need thereof, the method comprising:
a) reconstituting a reconstitutable, parenteral, pharmaceutical composition as disclosed herein in an infusion fluid selected from the group comprising of water, saline, potassium solution, glucose solution, glucose saline, dextrose solution, dextrose saline, balanced crystalloid solution, Hartmann's solution, Ringer's solution, lactated Ringer's solution, acetated Ringer's solution, Normosol-R, Normosol-M, Plasmalyte, plasma, human albumin, hydroxyethyl starch, dextran, whole blood, oxyglobin or a combination thereof; and
b) administering to the subject the reconstituted parenteral, pharmaceutical composition.

In a fourth aspect, the present invention provides a method for treating elevated intracranial pressure in a subject in need thereof, the method comprising administering to the subject a parenteral, pharmaceutical composition as disclosed herein.

In another embodiment, the method for treating elevated intracranial pressure is a method for treating traumatic brain injury.

In another embodiment, the method for treating elevated intracranial pressure is a method for treating stroke.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "about" or "approximately" as used herein means within an acceptable error range for the particular value as determined by one of ordinary skill in the art, which will depend in part on how the value is measured or determined, i.e., the limitations of the measurement system.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Unless defined otherwise, all technical and scientific terms used herein have the same meaning as commonly understood by those of ordinary skill in the art to which the invention belongs. For the purposes of the present invention, the following terms are defined below. "Alkyl" refers to monovalent alkyl groups which may be straight chained or branched and have from 1 to 4 carbon atoms or more preferably 1 to 3 carbon atoms. As used herein, $C_{1-4}$ alkyl refers to an alkyl selected from the group consisting of methyl, ethyl, n-propyl, iso-propyl, n-butyl, iso-butyl, sec-butyl and tert-butyl.

"Solubilisers" are substances that serve to aid the dissolution of an API. They may also be used to improve the solubilisation of the API and increase bioavailability. They may also be used to stabilize suspensions and prepare colloids and gels. Examples of solubilisers in injectable dosage forms include pH modifiers, water-soluble organic solvents, surfactants, water-insoluble organic solvents, medium-chain triglycerides, long-chain triglycerides, cyclodextrins, phospholipids, and the likes.

"Reconstitutable" refers to the ability to be restored or reconstructed to another state or semblance. This may occur via the addition of a liquid, for example adding water to a concentrate. A solid or a powder may also be reconstituted by dissolving the solid or powder in a liquid to form a solution. Accordingly, a concentrate, solution, dispersion, solid, powder or composition may be reconstituted to give its preferred usable form.

"Parenteral" means a mode of administration that occurs elsewhere in the body other than the mouth and the alimentary canal. Accordingly, parenteral administration is administration by delivery via routes other the gastrointestinal tract. As used herein, "parenteral" refers to modes of administration such as intramuscular, intravenous (bolus and/or infusion), subcutaneous, intravesical, or subgingival. In an embodiment, the mode of administration is intravenous.

In a first aspect, the present invention provides a reconstitutable, parenteral, pharmaceutical composition. In an embodiment, the reconstitutable, parenteral, pharmaceutical composition is in a form of a concentrate, solution, dispersion, solid, or powder. In another embodiment, the reconstitutable, parenteral, pharmaceutical composition is in a form of a concentrate. In this regard, the concentrate comprises a large amount of solutes (API and/or at least one of the aforementioned solubiliers). In another embodiment, the reconstitutable, parenteral, pharmaceutical composition is in a form of a solution. In another embodiment, the reconstitutable, parenteral, pharmaceutical composition is in a form of a dispersion. In another embodiment, the reconstitutable, parenteral, pharmaceutical composition is in a form of an aqueous dispersion. In another embodiment, the reconstitutable, parenteral, pharmaceutical composition is in a form of a oil dispersion. In another embodiment, the reconstitutable, parenteral, pharmaceutical composition is in a form of a solid. In another embodiment, the reconstitutable, parenteral, pharmaceutical composition is in a form of a freeze dried solid. In another embodiment, the reconstitutable, parenteral, pharmaceutical composition is in a form of a supercritical dried solid. In another embodiment, the reconstitutable, parenteral, pharmaceutical composition is in a form of a powder. In another embodiment, the reconstitutable, parenteral, pharmaceutical composition is in a form of a freeze dried powder. In another embodiment, the reconstitutable, parenteral, pharmaceutical composition is in a form of a supercritical dried powder. In another embodiment, the reconstitutable, parenteral, pharmaceutical composition is in a form of a lyophilised solid. In another embodiment, the reconstitutable, parenteral, pharmaceutical composition is in a form of a lyophilised powder.

The reconstitutable, parenteral, pharmaceutical composition comprises a compound of Formula (I) or a pharmaceutically acceptable salt, solvate or prodrug thereof:

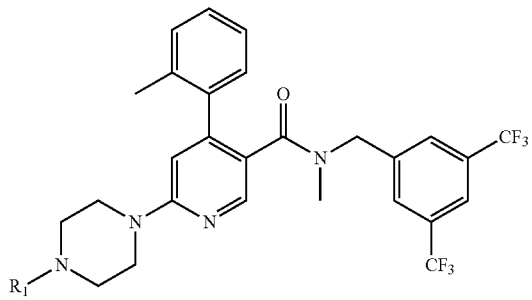

Formula (I)

wherein $R_1$ is H or $C_{1-4}$ alkyl.

In an embodiment, $R_1$ is H, methyl, ethyl, n-propyl, iso-propyl, n-butyl, sec-butyl, iso-butyl or tert-butyl. In another embodiment, $R_1$ is H, methyl, ethyl, n-propyl or iso-propyl. In another embodiment, $R_1$ is H. In another embodiment, $R_1$ is methyl. In another embodiment, $R_1$ is ethyl. In another embodiment, $R_1$ is n-propyl. In another embodiment, $R_1$ is iso-propyl. In another embodiment, $R_1$ is n-butyl. In another embodiment, $R_1$ is sec-butyl. In another embodiment, $R_1$ is iso-butyl. In another embodiment, $R_1$ is tert-butyl.

Accordingly, in some embodiments, the pharmaceutical composition comprises a compound of Formula (I) or a pharmaceutically acceptable salt, solvate or prodrug thereof selected from the following:

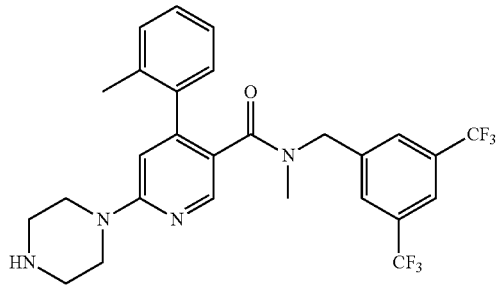

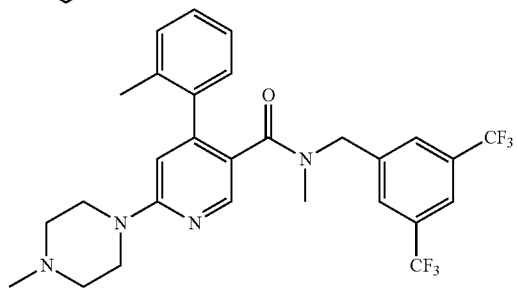

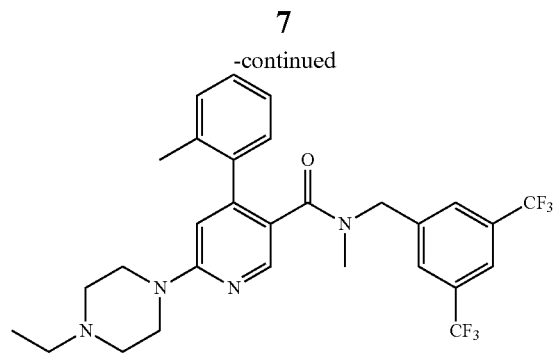
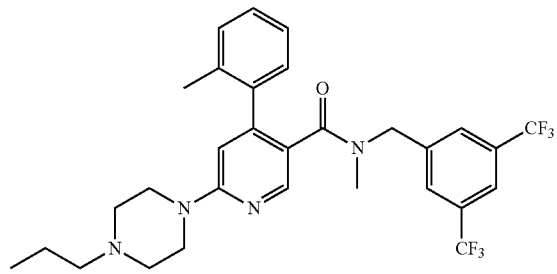
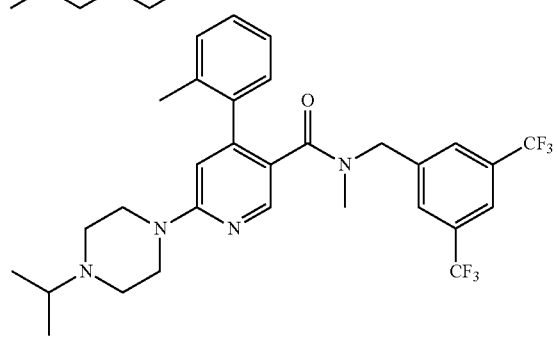
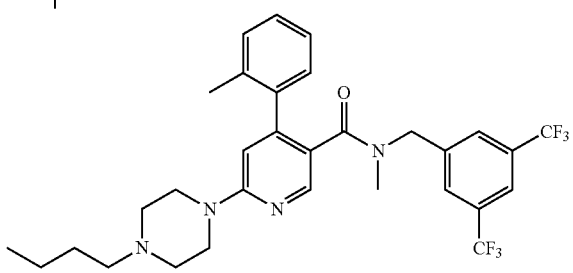
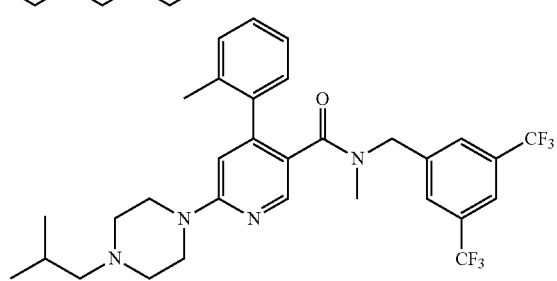
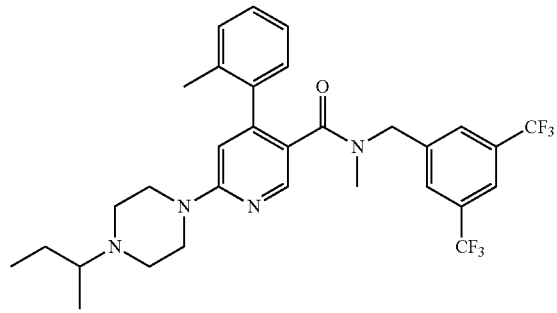

In particular, in some embodiments, the pharmaceutical composition comprises a compound of Formula (I) or a pharmaceutically acceptable salt, solvate or prodrug thereof which is:

(Ia)

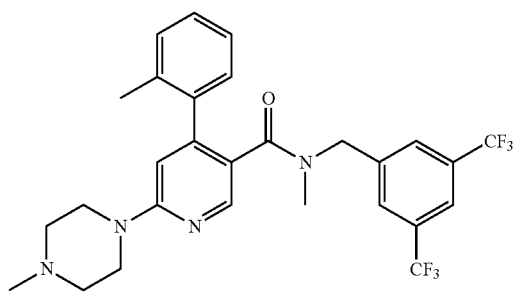

(Ib)

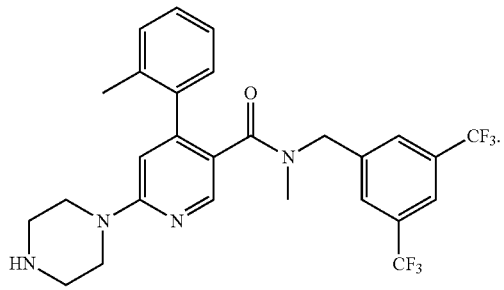

In an embodiment, compound of Formula (I) or a pharmaceutically acceptable salt, solvate or prodrug thereof is provided as a salt. In another embodiment, compound of Formula (I) or a pharmaceutically acceptable salt, solvate or prodrug thereof is a HCl salt. In another embodiment, compound of Formula (I) or a pharmaceutically acceptable salt, solvate or prodrug thereof is a 2 HCl salt. Accordingly, in some embodiments, the pharmaceutical composition comprises a compound of Formula (I) or a pharmaceutically acceptable salt, solvate or prodrug thereof selected from the following:

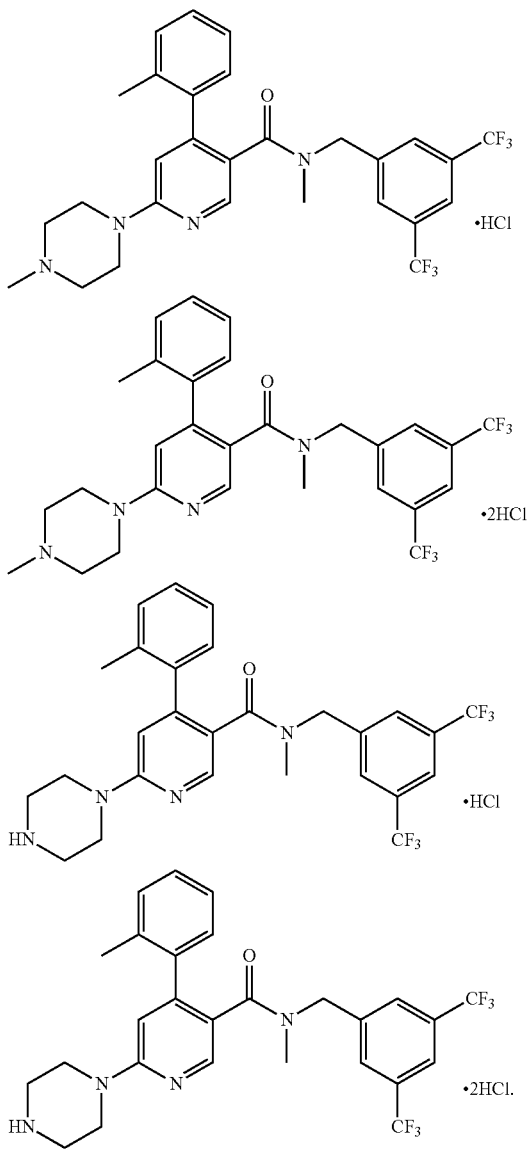

One important parameter of a parenteral formulation is the solubility of the API. It is desirable for the API to maintain its solubility over a long period of time for storage, or at least over the administration period. A formulation with poor dissolution of API would result in a lower bioavailability and can potentially increase the API toxicity as a larger dose would be required to deliver the same therapeutic effect. The solubility depends on a combination of various factors, such as the physio-chemical properties of the API (such as salt form, HLB, size and conformation, charges, complexation), the temperature and pressure, the pH, the type and amount of excipient used, complexation of API with excipient, etc. The inventors have found that an excipient is critical for maintaining compound of Formula (I) in the reconstitutable form and well as in the reconstituted form. In particular, a solubiliser. Even more favorably, a non-ionic solubiliser is preferred. Without wanting to be bound by theory, the inventors believe that the common ion effect is responsible for the reduction in the solubility of an ionic precipitate when a soluble compound containing one of the ions of the precipitate is added to the solution in equilibrium with the precipitate. If the concentration of any one of the ions is increased, then according to Le Chatelier's principle, some of the ions in excess should be removed from solution, by combining with the oppositely charged ions. Some of the salt will be precipitated until the ion product is equal to the solubility product.

Accordingly, the reconstitutable, parenteral, pharmaceutical composition comprises at least one solubiliser selected from the group comprising of glycerol, glycerin, dimethylacetamide, N-methyl-2-pyrrolidone, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), polysorbate 80 (Tween 80), castor oil, cottonseed oil, triglyceride, sesame oil, soybean oil, or safflower oil.

In an embodiment, with respect to the reconstitutable, parenteral, pharmaceutical composition, at least one solubiliser is selected from the group comprising of glycerol, glycerin, dimethylacetamide, N-methyl-2-pyrrolidone, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), or polysorbate 80 (Tween 80), In another embodiment, the at least one solubiliser is selected from the group comprising of castor oil, cottonseed oil, triglyceride, sesame oil, soybean oil, or safflower oil. In another embodiment, the at least one solubiliser is selected from the group comprising of glycerol, glycerin, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), or polysorbate 80 (Tween 80). In another embodiment, the at least one solubiliser is selected from the group comprising of propylene glycol, polyethylene glycol 300, polyethylene glycol 400, Kolliphor HS 15 (Solutol HS 15), Kolliphor EL. (Cremophor EL), Kolliphor 60 (Cremophor RH 60), or polysorbate 80 (Tween 80). In another embodiment, the solubiliser is propylene glycol. In another embodiment, the solubiliser is polyethylene glycol 300. In another embodiment, the solubiliser is polyethylene glycol 400. In another embodiment, the solubiliser is Kolliphor HS 15 (Solutol HS 15). In another embodiment, the solubiliser is Kolliphor EL (Cremophor EL). In another embodiment, the solubiliser is Kolliphor RH 60 (Cremophor RH 60). In another embodiment, the solubiliser is polysorbate 80 (Tween 80).

In an embodiment, with respect to the reconstitutable, parenteral, pharmaceutical composition, the at least one solubiliser is present in the composition in an amount of about 5% to about 99.8% wt/wt based on the total weight of the composition, In another embodiment, the amount is about 10% to about 99.8% wt/wt based on the total weight of the composition. In another embodiment, the amount is about 15% to about 99.8% wt/wt based on the total weight of the composition. In another embodiment, the amount is about 20% to about 99.8% wt/wt based on the total weight of the composition. In another embodiment, the amount is about 25% to about 99.8% wt/wt based on the total weight of the composition. In another embodiment, the amount is about 30% to about 99.8% wt/wt based on the total weight of the composition. In another embodiment, the amount is about 35% to about 99.8% wt/wt based on the total weight of the composition. In another embodiment, the amount is about 40% to about 99.8% wt/wt based on the total weight of the composition. In another embodiment, the amount is about 45% to about 99.8% wt/wt based on the total weight of the composition. In another embodiment, the amount is about 50% to about 99.8% wt/wt based on the total weight of the composition. In another embodiment, the amount is about 55% to about 99.8% wt/wt based on the total weight of the composition. In another embodiment, the amount is about 60% to about 99.8% wt/wt based on the total weight of the composition. In another embodiment, the amount is about 65% to about 99.8% wt/wt based on the total weight of the composition. In another embodiment, the amount is about 70% to about 99.8% wt/wt based on the total weight of the composition.

In an embodiment, with respect to the reconstitutable, parenteral, pharmaceutical composition, the compound of Formula (I) is present in the composition in an amount of about 0.2% to about 1.8% wt/wt based on the total weight of the composition. In another embodiment, the amount is about 0.25% to about 1.8% wt/wt based on the total weight of the composition. In another embodiment, the amount is about 0.25% to about 1.7% wt/wt based on the total weight of the composition. In another embodiment, the amount is about 0.3% to about 1.7% wt/wt based on the total weight of the composition. In another embodiment, the amount is about 0.3% to about 1.6% wt/wt based on the total weight of the composition. In another embodiment, the amount is about 0.35% to about 1.6% wt/wt based on the total weight of the composition. In another embodiment, the amount is about 0.35% to about 1.5% wt/wt based on the total weight of the composition. In another embodiment, the amount is about 0.4% to about 1.5% wt/wt based on the total weight of the composition. In another embodiment, the amount is about 0.4% to about 1.4% wt/wt based on the total weight of the composition. In another embodiment, the amount is about 0.45% to about 1.4% wt/wt based on the total weight of the composition. In another embodiment, the amount is about 0.45% to about 1.3% wt/wt based on the total weight of the composition. In another embodiment, the amount is about 0.5% to about 1.3% wt/wt based on the total weight of the composition. In another embodiment, the amount is about 0.5% to about 1.2% wt/wt based on the total weight of the composition.

In an embodiment, with respect to the reconstitutable, parenteral, pharmaceutical composition, the wt/wt ratio of compound of Formula (I) or a pharmaceutically acceptable salt, solvate or prodrug thereof to solubiliser is about 1:40 to about 1:250. In another embodiment, the wt/wt ratio is about 1:50 to about 1:250. In another embodiment, the wt/wt ratio is about 1:50 to about 1:240. In another embodiment, the wt/wt ratio is about 1:60 to about 1:240. in another embodiment, the wt/wt ratio is about 1:60 to about 1:230. In another embodiment, the wt/wt ratio is about 1:70 to about 1:230. In another embodiment, the wt/wt ratio is about 1:70 to about 1:220. In another embodiment, the wt/wt ratio is about 1:80 to about 1:220. In another embodiment, the wt/wt ratio is about 1:80 to about 1:210. In another embodiment, the wt/wt ratio is about 1:90 to about 1:210. in another embodiment, the wt/wt ratio is about 1:90 to about 1:200. In another embodiment, the wt/wt ratio is about 1:100 to about 1:200. In another embodiment, the wt/wt ratio is about 1:100 to about 1:190. In another embodiment, the wt/wt ratio is about 1:110 to about 1:190. In another embodiment, the wt/wt ratio is about 1:110 to about 1:180.

In an embodiment, the reconstitutable, parenteral, pharmaceutical composition is in a form of a concentrate, wherein compound of Formula (I) and at least one solubiliser comprise 100% of the total weight of the composition. In another embodiment, compound of Formula (I) and at least one solubiliser comprise about 99.8% of the total weight of the composition. In another embodiment, compound of Formula (I) and at least one solubiliser comprise about 99.5% of the total weight of the composition. In another embodiment, compound of Formula (I) and at least one solubiliser comprise about 99% of the total weight of the composition. In another embodiment, compound of Formula (I) and at least one solubiliser comprise about 98% of the total weight of the composition. In another embodiment, compound of Formula (I) and at least one solubiliser comprise about 97% of the total weight of the composition. In another embodiment, compound of Formula (I) and at least one solubiliser comprise about 96% of the total weight of the composition. In another embodiment, compound of Formula (I) and at least one solubiliser comprise about 95% of the total weight of the composition. In another embodiment, compound of Formula (I) and at least one solubiliser comprise about 90% of the total weight of the composition. In another embodiment, compound of Formula (I) and at least one solubiliser comprise about 85% of the total weight of the composition. In another embodiment, compound of Formula (I) and at least one solubiliser comprise about 80% of the total weight of the composition.

In an embodiment, the reconstitutable, parenteral, pharmaceutical composition is a reconstitutable, intravenous, pharmaceutical composition. In another embodiment, the composition is a reconstitutable, intravenous bolus, pharmaceutical composition. In another embodiment, the composition is a reconstitutable, intravenous infusion, pharmaceutical composition. In another embodiment, the composition is a reconstitutable, intramuscular, pharmaceutical composition. In another embodiment, the composition is a reconstitutable, subcutaneous, pharmaceutical composition. In another embodiment, the composition is a reconstitutable, intravesical, pharmaceutical composition. In another embodiment, the composition is a reconstitutable, subgingival, pharmaceutical composition.

In an embodiment, when the reconstitutable, parenteral pharmaceutical composition is a reconstitutable, intravenous, pharmaceutical composition, with at least one solubiliser selected from the group comprising of a glycerol, glycerin, dimethylacetamide, N-methyl-2-pyrrolidone, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), or polysorbate 80 (Tween 80). In another embodiment, with at least one solubiliser selected from the group comprising of a glycerol, glycerin, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), or polysorbate 80 (Tween 80). In another embodiment, the at least one solubiliser selected from the group comprising of a propylene glycol, polyethylene glycol 300, polyethylene glycol 400, Kolliphor HS 15 (Solutol HS 15), Kolliphor EL (Cremophor EL), Kolliphor RH 60 (Cremophor RH 60), or polysorbate 80 (Tween 80). In another embodiment, the solubiliser is propylene glycol. In another embodiment, the solubiliser is polyethylene glycol 300. In another embodiment, the solubiliser is polyethylene glycol 400. In another embodiment, the solubiliser is Kolliphor HS 15 (Solutol HS 15). In another embodiment, the solubiliser is Kolliphor EL (Cremophor EL). In another embodiment, the solubiliser is Kolliphor RH 60 (Cremophor RH 60). In another embodiment, the solubiliser is polysorbate 80 (Tween 80).

In an embodiment, with respect to the reconstitutable, intravenous, pharmaceutical composition, propylene glycol is present in the composition in an amount of about 40% to about 99.8% wt/wt based on the total weight of the composition. In another embodiment, the amount is of about 45% to about 99.8% wt/wt based on the total weight of the composition. In another embodiment, the amount is of about 50% to about 99.8% wt/wt based on the total weight of the composition. In another embodiment, the amount is of about 55% to about 99.8% wt/wt based on the total weight of the composition. In another embodiment, the amount is of about 60% to about 99.8% wt/wt based on the total weight of the composition. In another embodiment, the amount is of about 65% to about 99.8% wt/wt based on the total weight of the composition. In another embodiment, the amount is of about 70% to about 99.8% wt/wt based on the total weight of the composition. In another embodiment, the amount is of about 75% to about 99.8% wt/wt based on the total weight of the composition. In another embodiment, the amount is of about 80% to about 99.8% wt/wt based on the total weight of the composition.

In an embodiment, and with respect to the reconstitutable, intravenous pharmaceutical composition, the composition is maintained at a pH of between about 3 to about 7. In another embodiment, the composition is maintained at a pH of between about 3:5 to about 7. In another embodiment, the composition is maintained at a pH of between about 3.5 to about 6.5. In another embodiment, the composition is maintained at a pH of between about 4 to about 7. In another embodiment, the composition is maintained at a pH of between about 4 to about 6.5. In another embodiment, the composition is maintained at a pH of between about 4.5 to about 6.5. In another embodiment, the composition is maintained at a pH of between about 4.5 to about 6. In another embodiment, the composition is maintained at a pH of about 4.5. In another embodiment, the composition is maintained at a pH of about 5. In another embodiment, the composition is maintained at a pH of about 5.5. In another embodiment, the composition is maintained at a pH of about 6. In another embodiment, the composition is maintained at a pH of about 6.5.

It would be understood by the skilled person that another solubiliser as described herein may be added to the reconstitutable, parenteral, pharmaceutical composition to form a second reconstitutable, parenteral, pharmaceutical composition. For example, a lypholised powder (reconstitutable, parenteral, pharmaceutical composition) may be reconstituted with propylene glycol to form a concentrate or a solution (second reconstitutable, parenteral, pharmaceutical composition). The second reconstitutable, parenteral, pharmaceutical composition may then be further reconstituted or diluted with an infusion fluid to give a parenteral, pharmaceutical composition. Such would be within the scope of the invention.

Accordingly, in a second aspect, the present invention provides a parenteral, pharmaceutical composition comprising:
(i) a compound of Formula (I) or a pharmaceutically acceptable salt, solvate or prodrug thereof:

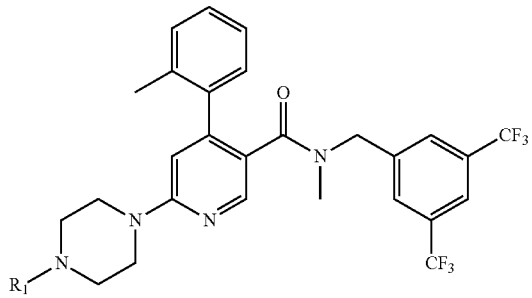

Formula (I)

wherein $R_1$ is H or $C_{1-4}$ alkyl; and
(ii) at least one solubiliser selected from the group comprising of a glycerol, glycerin, dimethylacetamide, N-methyl-2-pyrrolidone, propylene glycol, polyethylene glycol 300, polyethylene glycol 400, ricinoleate based solubiliser, cyclodextrin, Kolliphor HS 15 (Solutol HS 15), Kolliphor EL (Cremophor EL), Kolliphor RH 60 (Cremophor RH 60), polysorbate 80 (Tween 80), castor oil, cottonseed oil, triglyceride, sesame oil, soybean oil, or safflower oil; and
(iii) an infusion fluid selected from the group comprising of water, saline, potassium solution, glucose solution, glucose saline, dextrose solution, dextrose saline, balanced crystalloid solution, Hartmann's solution, Ringer's solution, lactated Ringer's solution, acetated Ringer's solution, Normosol-R, Normosol-M, Plasmalyte, plasma, human albumin, hydroxyethyl starch, dextran, whole blood, oxyglobin or a combination thereof.

In this regard, the reconstitutable, parenteral pharmaceutical composition may be reconstituted in an infusion fluid to form the parenteral pharmaceutical composition.

Osmotic concentration, formerly known as osmolarity, is the measure of solute concentration, defined as the number of osmoles (Osm) of solute per litre (L) of solution (osmol/L or Osm/L). Normal osmolarity of blood/serum is about 300-310 mOsm/L. The tonicity of an intravenous fluid may dictate whether the solution should be delivered via the peripheral or central venous route. Hypotonic and hypertonic solutions may be infused in small volumes and into large vessels, where dilution and distribution are rapid. Solutions differing greatly from the normal range may cause tissue irritation, pain on injection, and electrolyte shifts. When solutions with extremes of tonicity are infused, fluids shift into or out of cells, including endothelial cells of the tunica intima near the catheter tip and blood cells. The resulting changes in the cell size of the vein wall causes inflammatory and clotting processes to occur, leading to phlebitis and thrombophlebitis. Accordingly, it is critical that the osmolarity of the parenteral, pharmaceutical composition be regulated properly. The inventors have found that the use of certain infusion fluids and in certain ratios with respect to the stabiliser may result in the osmolarity range of the parenteral, pharmaceutical composition being desirable.

In an embodiment, with respect to the parenteral, pharmaceutical composition, the infusion fluid is selected from the group comprising of water, saline, potassium solution, glucose (dextrose) solution, glucose saline, Hartmann's solution, Ringer's solution, lactated Ringer's solution, acetated Ringer's solution, Normosol-R, Normosol-M, or a combination thereof. In another embodiment, the infusion fluid is water. In another embodiment, the infusion fluid is saline. In another embodiment, the infusion fluid is potassium solution. In another embodiment, the infusion fluid is glucose (dextrose) solution. In another embodiment, the infusion fluid is glucose saline. In another embodiment, the infusion fluid is Hartmann's solution. In another embodiment, the infusion fluid is Ringer's solution. In another embodiment, the infusion fluid is lactated Ringer's solution. In another embodiment, the infusion fluid is acetated Ringer's solution. In another embodiment, the infusion fluid is Normosol-R. In another embodiment, the infusion fluid is Normosol-M.

In another embodiment, the infusion fluid is 5% glucose (dextrose) solution.

In an embodiment, with respect to the parenteral, pharmaceutical composition, the composition has an osmolality of about 100 mOsm/kg to about 700 mOsm/kg. In another embodiment, the composition has an osmolality of about 200 mOsm/kg to about 600 mOsm/kg. In another embodiment, the composition has an osmolality of about 200 mOsm/kg to about 550 mOsm/kg. In another embodiment, the composition has an osmolality of about 200 mOsm/kg to about 500 mOsm/kg. In another embodiment, the composition has an osmolality of about 200 mOsm/kg to about 450 mOsm/kg. In another embodiment, the composition has an osmolality of about 200 mOsm/kg to about 400 mOsm/kg. In another embodiment, the composition has an osmolality of about 250 mOsm/kg to about 650 mOsm/kg. In another embodiment, the composition has an osmolality of about 300 mOsm/kg to about 650 mOsm/kg. In another embodiment, the composition has an osmolality of about 350 mOsm/kg to about 650 mOsm/kg. In another embodiment, the composition has an osmolality of about 400 mOsm/kg to about 650 mOsm/kg. In another embodiment, the composition has an osmolality of about 450 mOsm/kg to about 650 mOsm/kg.

Notwithstanding the need for controlling Osmolarity the inventors discovered that not every infusion fluid may be suitable for administration due to the risk of transient haemolysis during infusion. For instance, the undesirable effect can be prevented by using an infusion solution consisting of 5% glucose. Hence due to the specific osmolarity of the compound as well as due to the need to prevent transient haemolysis during infusion, an optimal infusion solution is achieved by diluting the stock solution in 5% glucose. A lower glucose concentration may increase the risk of haemolysis while on the other hand a much higher glucose solution may generate a too high osmolarity.

In an embodiment, with respect to the parenteral, pharmaceutical composition, the wt/wt ratio of compound of Formula (I) or a pharmaceutically acceptable salt, solvate or prodrug thereof to solubiliser is about 1:40 to about 1:250. In another embodiment, the wt/wt ratio is about 1:50 to about 1:250. In another embodiment, the wt/wt ratio is about 1:50 to about 1:240. In another embodiment, the wt/wt ratio is about 1:60 to about 1:240. In another embodiment, the wt/wt ratio is about 1:60 to about 1:230. In another embodiment, the wt/wt ratio is about 1:70 to about 1:230. In another embodiment, the wt/wt ratio is about 1:70 to about 1:220. In another embodiment, the wt/wt ratio is about 1:80 to about 1:220. In another embodiment, the wt/wt ratio is about 1:80 to about 1:210. In another embodiment, the wt/wt ratio is about 1:90 to about 1:210. In another embodiment, the wt/wt ratio is about 1:90 to about 1:200. In another embodiment, the wt/wt ratio is about 1:100 to about 1:200. In another embodiment, the wt/wt ratio is about 1:100 to about 1:190. In another embodiment, the wt/wt ratio is about 1:110 to about 1:190. In another embodiment, the wt/wt ratio is about 1:110 to about 1:180.

In an embodiment, with respect to the parenteral, pharmaceutical composition, the wt/wt ratio of the at least one solubiliser to the infusion fluid is about 1:5 to about 1:2100. In another embodiment, the wt/wt ratio is about 1:10 to about 1:2000. In another embodiment, the wt/wt ratio is about 1:10 to about 1:1900. In another embodiment, the wt/wt ratio is about 1:20 to about 1:1900. In another embodiment, the wt/wt ratio is about 1:20 to about 1:1800. In another embodiment, the wt/wt ratio is about 1:30 to about 1:1800. In another embodiment, the wt/wt ratio is about 1:30 to about 1:1700. In another embodiment, the wt/wt ratio is about 1:40 to about 1:1700. In another embodiment, the wt/wt ratio is about 1:40 to about 1:1600. In another embodiment, the wt/wt ratio is about 1:50 to about 1:1600.

In an embodiment, with respect to the parenteral, pharmaceutical composition, the composition is maintained at a pH of between about 3 to about 7. In another embodiment, the composition is maintained at a pH of between about 3.5 to about 7. In another embodiment, the composition is maintained at a pH of between about 3.5 to about 6.5. In another embodiment, the composition is maintained at a pH of between about 4 to about 7. In another embodiment, the composition is maintained at a pH of between about 4 to about 6.5. In another embodiment, the composition is maintained at a pH of between about 4.5 to about 6.5. In another embodiment, the composition is maintained at a pH of between about 4.5 to about 6. In another embodiment, the composition is maintained at a pH of about 4.5. In another embodiment, the composition is maintained at a pH of about 5. In another embodiment, the composition is maintained at a pH of about 5.5. In another embodiment, the composition is maintained at a pH of about 6. In another embodiment, the composition is maintained at a pH of about 6.5.

In an embodiment, the parenteral, pharmaceutical composition is an intravenous, pharmaceutical composition. In another embodiment, the composition is an intravenous bolus, pharmaceutical composition, In another embodiment, the composition is an intravenous infusion, pharmaceutical composition. In another embodiment, the composition is an intramuscular, pharmaceutical composition. In another embodiment, the composition is a subcutaneous, pharmaceutical composition. In another embodiment, the composition is an intravesical, pharmaceutical composition. In another embodiment, the composition is a subgingival, pharmaceutical composition.

In an embodiment, the reconstitutable, parenteral, pharmaceutical composition or parenteral, pharmaceutical composition is subjected to sterilisation. In another embodiment, the composition is subjected to gamma radiation. In another embodiment, the composition is subjected to heat treatment. In another embodiment, the composition is subjected to moist heat treatment. For example, the composition may be heat treated at about 140° C., about 130° C., about 120° C., about 110° C., about 100° C., or about 90° C. The composition may be heat treated for about 5 min, about 10 min, about 15 min, about 20 min, about 30 min, about 40 min. about 50 min, about 60 min or about 120 min.

In a third aspect, the present invention provides a method for treating elevated intracranial pressure in a subject in need thereof, the method comprising:
a) reconstituting a reconstitutable, parenteral, pharmaceutical composition as described herein in an infusion fluid selected from the group comprising of water, saline, potassium solution, glucose (dextrose) solution, glucose saline, balanced crystalloid solution, Hartmann's solution, Ringer's solution, lactated Ringer's solution, acetated Ringer's solution, Normosol-R, Normosol-M, Plasmalyte, plasma, human albumin, hydroxyethyl starch, dextran, whole blood, oxyglobin or a combination thereof; and b) administering to the subject the reconstituted parenteral, pharmaceutical composition.

In a fourth aspect, the present invention provides a method for treating elevated intracranial pressure in a subject in need thereof, the method comprising administering to the subject a parenteral, pharmaceutical composition as described herein.

In one embodiment, the dosage of the pharmaceutical composition administered to a subject in the various embodiments of the present invention is such that compound of Formula (I) is administered in the range from 0.1 mg/kg to 100 mg/kg. In one embodiment, the dosage of the pharmaceutical composition administered to a subject in the various embodiments of the present invention is such that compound of Formula (I) is administered in the range from 0.1 mg/kg to 100 mg/kg. For instance, the dosage amount may be 0.1 mg/kg, 0.2 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 10 mg/kg, 17.0 mg/kg, 18.0 mg/kg, 19.0 mg/kg, 20.0 mg/kg, 21.0 mg/kg, 22.0 mg/kg, 23.0 mg/kg, 24.0 mg/kg, 25.0 mg/kg, 26.0 mg/kg, 27.0 mg/kg, 28.0 mg/kg, 29.0 mg/kg, 30.0 mg/kg, 31.0 mg/kg, 32.0 mg/kg, 33.0 mg/kg, 34.0 mg/kg, 35.0 mg 36.0 mg/kg, 37.0 mg/kg, 38.0 mg/kg, 39.0 mg/kg, 40.0 mg/kg, 41.0 mg/kg, 42.0 mg/kg, 43.0 mg/kg, 44.0 mg/kg, 45.0 mg/kg, 46.0 mg/kg, 47.0 mg/kg, 48.0 mg/kg, 49.0 mg/kg, 50.0 mg/kg, 51.0 mg/kg, 52.0 mg/kg, 53.0 mg/kg, 54.0 mg/kg, 55.0 mg/kg, 56.0 mg/kg, 57.0 mg/kg, 58.0 mg/kg, 59.0 mg/kg, 60.0 mg/kg, 61.0 mg/kg, 62.0 mg/kg, 63.0 mg/kg, 64.0 mg/kg, 65.0 mg/kg, 66.0 mg/kg, 67.0 mg/kg, 68.0 mg/kg, 69.0 mg/kg, 70.0 mg/kg, 71.0 mg/kg, 72.0 mg/kg, 73.0 mg/kg, 74.0 mg/kg, 75.0 mg/kg, 76.0 mg/kg, 77.0 mg/kg, 78.0 mg/kg, 79.0 mg/kg, 80.0 mg/kg, 81.0 mg/kg, 82.0 mg/kg, 83.0 mg/kg, 84.0 mg/kg, 85.0 mg/kg, 86.0 mg/kg, 87.0 mg/kg, 88.0 mg/kg, 89.0 mg/kg, 90.0 mg/kg, 91.0 mg/kg, 92.0 mg/kg, 93.0 mg/kg, 94.0 mg/kg, 95.0 mg/kg, 96.0 mg/kg, 97.0 mg/kg, 98.0 mg/kg, or 99.0 mg/kg.

In an embodiment, the method for treating elevated intracranial pressure is a method for treating traumatic brain injury.

In another embodiment, the method for treating elevated intracranial pressure is a method for treating stroke.

In an embodiment the pharmaceutical composition shall be administered as a treatment for injury associated with concussion post the injury event.

In an embodiment the effective amount is an amount which is able to maintain the blood concentration of the compound of formula (I), or a pharmaceutically acceptable salt, solvate, or prodrug thereof, in the therapeutic range for at least 1 day for instance, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, or at least 20 days.

In an embodiment the effective amount is administered as a single or multiple dose. In an embodiment the effective amount is administered as a single or multiple oral dose.

The terms "treat," "treatment," and "treating" refer to one or more of the following:

(a) relieving or alleviating at least one symptom of a disorder in a subject, including for example, reducing intracranial pressure in a TBI patient;

(b) relieving or alleviating the intensity and/or duration of a manifestation of a disorder experienced by a subject including, but not limited to, those that are in response to a given stimulus (e.g., pressure, tissue injury, cold temperature, etc.); and (c) arresting, delaying the onset (i.e., the period prior to clinical manifestation of a disorder) and/or reducing the risk of developing or worsening a disorder.

A subject or patient in whom administration of the therapeutic compound is an effective therapeutic regimen for a disease or disorder is preferably a human.

Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts may be prepared by reaction of a compound with the appropriate inorganic or organic acid via any of a number of known methods. Alternatively, alkali and alkaline earth metal salts can be prepared by reacting a compound with the appropriate base via a variety of known methods. The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

The composition may contain any other suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

For example, the pharmaceutical composition may further comprise a preservative, a buffer, stabiliser and/or a viscosity enhancing agent. Examples of suitable preservatives are benzoic acid esters of para-hydroxybenzoic acid, phenols, phenylethyl alchohol or benzyl alcohol. Examples of suitable buffers are sodium phosphate salts, citric acid, tartaric acid and the like. Examples of suitable stabilisers are, antioxidants such as alpha-tocopherol acetate, alpha-thioglycerin, sodium metabisulphite, ascorbic acid, acetylcysteine, 8-hydroxyquinoline, chelating agents such as disodium edentate. Examples of suitable viscosity enhancing agents, suspending or dispersing agents are substituted cellulose ethers, substituted cellulose esters, polyvinyl alchohol, polyvinylpyrrolidone, carbomer, polyoxypropylene glycols, and sorbitan sesquioleate.

For example, the pharmaceutical composition may further comprise a pH controller. Examples of suitable pH controllers include hydrochloric acid, sodium hydroxide and the like.

It will be appreciated that any compound that is a prodrug of a compound of formula (I) is also within the scope and spirit of the invention. The term "pro-drug" is used in its broadest sense and encompasses those derivatives that are converted in vivo to the compounds of the invention. Such derivatives would readily occur to those skilled in the art, and include, for example, phosphoric acid derivatives.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Characterisation of Active Pharmaceutical Ingredient (API)

Compound of Formula (I), in particular compound (Ia) as shown below, is used in all examples, and in particular the 2 HCl salt of compound (Ia) (Compound (Ia) HCl).

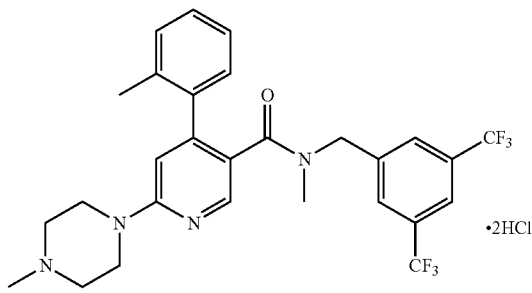 [SMILES: Cc1ccccc1-c1cc(N2CCN(C)CC2)ncc1C(=O)N(C)Cc1cc(C(F)(F)F)cc(C(F)(F)F)c1]

Solubility

Table 1 shows a solubility assessment of compound (Ia) and its respective pH. Ethanol was also assessed as part of this study. The API was freely soluble at a concentration of 50 mg/mL of Compound (Ia) HCl, where a golden yellow colour was observed.

TABLE 1

Solubility of Compound (Ia) 2HCl in Water

| Weight of Compound (Ia) HCl (mg) | Volume of Water (mL) | Concentration (mg/mL) | Result | Appearance of solution | pH |
|---|---|---|---|---|---|
| 50 | 10 | 5 | Very soluble | Light yellow | 2.39 |
| 100 | 10 | 10 | Very soluble | Light yellow | 2.14 |
| 150 | 10 | 15 | Soluble | Light yellow | 2.02 |
| 200 | 10 | 20 | Soluble | Yellow | 1.87 |
| 250 | 10 | 25 | Soluble | Yellow | 1.81 |
| 300 | 10 | 30 | Soluble | Yellow | 1.75 |
| 350 | 10 | 35 | Soluble | Yellow | 1.72 |
| 400 | 10 | 40 | Soluble | Gold yellow | 1.66 |
| 450 | 10 | 45 | Soluble | Gold yellow | 1.54 |
| 500 | 10 | 50 | Soluble | Gold yellow | 1.52 |

The co-solvents considered and the solubility results are listed in Table 2. After seven days the solutions were checked again and solution 1 and 2 were found to have remained as their initial appearance.

TABLE 2

Solubility of 50 mg/mL Compound (Ia) 2HCl with Kolliphor HS 15 and Tween 80

| Solution Sample # | Co-Solvent | Concentration mg/mL | Appearance | pH | Soluble | Stable after 4 hours | Stable after 6 hours |
|---|---|---|---|---|---|---|---|
| 1 | Kolliphor HS 15 | 250 mg/mL | Clear, homogeneous, yellow | 1.48 | Yes | Yes | Yes |
| 2 | Kolliphor HS 15 | 200 mg/mL | Clear, homogeneous, yellow | 1.51 | Yes | Yes | Yes |
| 3 | Kolliphor HS 15 | 150 mg/mL | Clear, homogeneous, yellow | 1.47 | Yes | Yes | Yes |

TABLE 2-continued

Solubility of 50 mg/mL Compound (Ia) 2HCl with Kolliphor HS 15 and Tween 80

| Solution Sample # | Co-Solvent | Concentration mg/mL | Appearance | pH | Soluble | Stable after 4 hours | Stable after 6 hours |
|---|---|---|---|---|---|---|---|
| 4 | Kolliphor HS 15 | 100 mg/mL | Clear, homogeneous, yellow | 1.51 | Yes | Yes | Little crystals |
| 5 | Kolliphor HS 15 | 50 mg/mL | Clear, homogeneous, yellow | 1.53 | Yes | Little crystals | Crystals |
| 6 | Tween 80 | 250 mg/mL | Clear, homogeneous, yellow | 1.56 | Yes | Yes | Yes |

Excipient Compatibility

The successful formulation characteristics of a solution are its solubility and stability. The solvent system chosen must also be able to solubilise the drug at the desired concentration and must provide an environment where the drug has sufficient chemical stability. This study is an initial comparison of 2 weeks stability with potential excipients, and the % degradation was assessed. The excipients assessed are those typically found in liquid and freeze dried formulations. Excipient compatibility was investigated by subjecting a series of mixes containing active and excipient to elevated temperature for a nominated period and monitoring any degradation.

TABLE 3

Excipients in Solubility Trials

| Formulation | Appearance |
|---|---|
| 5% glucose (dextrose) | Light yellow, homogeneous and clear liquid. |
| 0.9% NaCl | Light yellow, homogeneous and clear liquid. |
| Sodium Acetate (anhydrous)164 mg/mL | Insoluble. |
| Sodium Hydroxide pH 3 | Light yellow, homogeneous and clear liquid. |
| Sodium Hydroxide pH 4 | Light yellow, homogeneous and clear liquid. |
| Sodium Hydroxide pH 5 | Light yellow, homogeneous and clear liquid. |
| Sodium Hydroxide pH 6 | Light yellow, homogeneous and clear liquid. |
| Sodium Hydroxide pH 7 | Light yellow, homogeneous and clear liquid. |
| Sodium Hydroxide pH 8 | Light yellow, homogeneous and clear liquid. |
| Sodium Hydroxide pH 9 | Light yellow, homogeneous and clear liquid. |
| Sodium Hydroxide pH 10 | Light yellow, homogeneous and clear liquid. |
| Sodium Phosphate Monohydrate (276 mg/mL) | Insoluble. |
| Dibasic Sodium Phosphate (142 mg/mL) | Insoluble. |
| Sodium Citrate (26 mg/mL) | Light yellow, homogeneous and clear liquid. |
| Sodium bicarbonate(50 mg/mL) | Insoluble. |
| Sodium sulphite (1 mg/mL) | Light yellow, homogeneous and clear liquid. |
| Mannitol (200 mg/mL) | Insoluble. |
| Sucrose (200 mg/mL) | Light yellow, homogeneous and clear liquid. |
| Kolliphor | Light yellow, homogeneous and clear liquid. |
| L-Arginine (100 mg/mL) | Insoluble. |

The solutions that were soluble in Table 3 were also prepared using Kolliphor 400 mg/mL in water and with Tween 80 as a solubiliser. These solutions were placed on stability at 25° C./60% RH and 40° C./75% RH for 14 days. The formulations was assessed for assay and related substances after 14 days of storage. Refer to Table 4 and 5 for the results.

TABLE 4

% Assay Results for Each Formulation

| Formulation Description | Initial | After 14 days at 25 C./60% RH | After 14 days at 40 C./75% RH |
|---|---|---|---|
| 5% dextrose-250 mg/mL Kolliphor | 102.8 | 105.1 | 97.5 |
| 0.9% NaCl-250 mg/mL Kolliphor | 102.0 | 99.7 | 98.1 |
| NaOH pH 3-250 mg/mL Kolliphor | 100.7 | 97.5 | 97.9 |
| NaOH pH 4-250 mg/mL Kolliphor | 104.7 | 98.8 | 97.6 |
| NaOH pH 5-250 mg/mL Kolliphor | 104.1 | 98.9 | 98.0 |
| NaOH pH 6-250 mg/mL Kolliphor | 102.2 | 98.3 | 98.4 |
| NaOH pH 7-250 mg/mL Kolliphor | 101.7 | 98.1 | 100.5 |
| NaOH pH 8-250 mg/mL Kolliphor | 100.8 | 96.9 | 96.8 |
| NaOH pH 9-250 mg/mL Kolliphor | 101.9 | 98.1 | 99.0 |
| NaOH pH 10-250 mg/mL Kolliphor | 99.0 | 95.6 | 96.3 |
| Sodium Citrate-250 mg/mL Kolliphor | 103.9 | 98.4 | 99.7 |
| Sodium sulphite-250 mg/mL Kolliphor | 93.7 | 90.2 | 92.5 |
| Sucrose-250 mg/mL Kolliphor | 102.2 | 98.2 | 97.2 |
| Kolliphor-250 mg/mL Kolliphor | 102.1 | 98.7 | 99.0 |
| 5% dextrose-400 mg/mL Kolliphor | 103.3 | 97.4 | 97.3 |
| 0.9% NaCl-400 mg/mL Kolliphor | 104.1 | 98.8 | 96.7 |
| Kolliphor-400 mg/mL Kolliphor | 104.8 | 98.6 | 98.2 |
| NaOH pH 3-400 mg/mL Kolliphor | 104.2 | 95.9 | 92.5 |
| NaOH pH 4-400 mg/mL Kolliphor | 101.0 | 96.1 | 94.3 |
| NaOH pH 5-400 mg/mL Kolliphor | 101.3 | 97.4 | 94.8 |
| NaOH pH 6-400 mg/mL Kolliphor | 101.6 | 97.8 | 96.3 |
| NaOH pH 7-400 mg/mL Kolliphor | 102.9 | 97.6 | 96.7 |
| NaOH pH 8-400 mg/mL Kolliphor | 102.3 | 96.7 | 96.8 |
| NaOH pH 9-400 mg/mL Kolliphor | 100.6 | 96.1 | 95.1 |
| NaOH pH 10-400 mg/mL Kolliphor | 100.2 | 95.5 | 95.4 |
| Sodium Citrate-400 mg/mL Kolliphor | 102.8 | 97.0 | 97.3 |

TABLE 4-continued

% Assay Results for Each Formulation

| Formulation Description | Initial | After 14 days at 25 C./60% RH | After 14 days at 40 C./75% RH |
|---|---|---|---|
| Sodium sulphite-400 mg/mL Kolliphor | 94.2 | 90.8 | 94.1 |
| Sucrose-400 mg/mL Kolliphor | 105.0 | 96.2 | 95.8 |
| Tween 80-250 mg/mL | 102.7 | 97.9 | 97.1 |

TABLE 5

% Impurity Results for Each Formulation

| Formulation Description | Initial % Total | Initial % Major | After 14 days at 25° C./60% RH % Total | After 14 days at 25° C./60% RH % Major | After 14 days at 40° C./75% RH % Total | After 14 days at 40° C./75% RH % Major |
|---|---|---|---|---|---|---|
| 5% Dextrose [1] | 1.09 | 0.47 | 1.10 | 0.15 | 1.78 | 0.56 |
| 0.9% NaCl [1] | 1.09 | 0.47 | 1.16 | 0.17 | 1.46 | 0.32 |
| NaOH pH 3 [1] | 1.09 | 0.48 | 1.16 | 0.21 | 2.37 | 1.13 |
| NaOH pH 4 [1] | 1.08 | 0.47 | 1.29 | 0.45 | 4.24 | 2.98 |
| NaOH pH 5 [1] | 1.12 | 0.51 | 1.28 | 0.41 | 2.59 | 1.58 |
| NaOH pH 6 [1] | 1.13 | 0.52 | 1.14 | 0.22 | 1.27 | 0.33 |
| NaOH pH 7 [1] | 1.14 | 0.53 | 1.13 | 0.23 | 1.29 | 0.36 |
| NaOH pH 8 [1] | 1.15 | 0.54 | 1.15 | 0.25 | 1.41 | 0.48 |
| NaOH pH 9 [1] | 1.14 | 0.53 | 1.09 | 0.23 | 1.34 | 0.41 |
| NaOH pH 10 [1] | 1.15 | 0.54 | 1.09 | 0.21 | 1.31 | 0.36 |
| Sodium Citrate [1] | 1.11 | 0.51 | 1.06 | 0.16 | 1.21 | 0.29 |
| Sodium Sulphite [1] | 10.40 | 9.84 | 10.50 | 6.43 | 8.74 | 4.13 |
| Sucrose [1] | 1.16 | 0.56 | 1.20 | 0.2 | 2.05 | 0.39 |
| Kolliphor-250 mg/mL | 1.10 | 0.51 | 1.13 | 0.18 | 2.36 | 0.87 |
| 5% Dextrose [2] | 1.08 | 0.5 | 1.17 | 0.21 | 1.72 | 0.53 |
| 0.9% NaCl [2] | 1.07 | 0.49 | 1.25 | 0.25 | 2.17 | 0.86 |
| Kolliphor [2] | 1.07 | 0.49 | 1.21 | 0.24 | 2.04 | 0.83 |
| NaOH pH 3 [2] | 1.07 | 0.49 | 1.22 | 0.24 | 2.01 | 0.78 |
| NaOH pH 4 [2] | 1.10 | 0.51 | 1.22 | 0.33 | 3.32 | 2.20 |
| NaOH pH 5 [2] | 1.11 | 0.51 | 1.14 | 0.26 | 2.75 | 1.75 |
| NaOH pH 6 [2] | 1.09 | 0.51 | 1.03 | 0.15 | 1.23 | 0.26 |
| NaOH pH 7 [2] | 1.10 | 0.52 | 1.10 | 0.17 | 1.27 | 0.29 |
| NaOH pH 8 [2] | 1.10 | 0.52 | 1.10 | 0.19 | 1.28 | 0.32 |
| NaOH pH 9 [2] | 1.13 | 0.53 | 1.09 | 0.19 | 1.27 | 0.32 |
| NaOH pH 10 [2] | 1.12 | 0.54 | 1.10 | 0.19 | 1.30 | 0.33 |
| Sodium Citrate [2] | 1.13 | 0.52 | 1.12 | 0.19 | 1.28 | 0.33 |
| Sodium Sulphite [2] | 11.47 | 10.95 | 9.05 | 6.01 | 5.53 | 0.31 |
| Sucrose [2] | 1.18 | 0.6 | 1.37 | 0.32 | 1.46 | 0.26 |
| Tween 80-250 mg/mL | 1.08 | 0.52 | 0.98 | 0.15 | 1.16 | 0.19 |

[1] = 250 mg/mL Kolliphor
[2] = 400 mg/mL Kolliphor

The results indicate the Compound (Ia) 2 HCl was quite stable in a range of formulations. Compound (Ia) 2 HCl is more stable at pH 6 to 10 with regards to impurities results, however, during preparation it was observed that the solutions were easy to stabilise between pH 3 to 7. The solutions were also found to be stable in Kolliphor HS formulations at 250 mg/mL, 400 mg/mL and Tween 80 at 250 mg/mL in water.

Formulation Development—Part 1

Formulations were tested to establish an isotonic solution and also to establish the maximum concentration of Compound (Ia) 2 HCl. Formulations using Tween 80 and Kolliphor HS 15 as solubilisers at 250 mg/mL and a range of API concentrations were prepared. The concentration ranges were prepared to demonstrate the possible strengths recommended for the final formulation. In order to improve the tonicity, sodium chloride (NaCl) was added to the formulations. In addition, three other formulations were prepared, in which two contained the maximum concentration of Compound (Ia) 2 HCl at 50 mg/mL. The concentration of Tween 80 was also adjusted to verify the lower concentration range of solubiliser that could be used without losing formulation stability. The formulations are listed in Table 6 and these formulations were placed in stability chambers at 25° C./60% RH and 40° C./75% RH for 14 days.

TABLE 6

Formulations for Additional Stability Work

| F# | Formulation per mL |
|---|---|
| 1 | 5 mg Compound (Ia) 2HCl, 250 mg Tween 80, 9 mg/mL NaCl, adjust to pH 7 |
| 2 | 10 mg Compound (Ia) 2HCl, 250 mg Tween 80, 9 mg/mL NaCl, adjust to pH 7 |

TABLE 6-continued

Formulations for Additional Stability Work

| F# | Formulation per mL |
|---|---|
| 3 | 15 mg Compound (Ia) 2HCl, 250 mg Tween 80, 9 mg/mL NaCl, adjust to pH 7 |
| 4 | 20 mg Compound (Ia) 2HCl, 250 mg Tween 80, 9 mg/mL NaCl, adjust to pH 7 |
| 5 | 25 mg Compound (Ia) 2HCl, 250 mg Tween 80, 9 mg/mL NaCl, adjust to pH 7 |
| 6 | 30 mg Compound (Ia) 2HCl, 250 mg Tween 80, 9 mg/mL NaCl, adjust to pH 7 |
| 7 | 35 mg Compound (Ia) 2HCl, 250 mg Tween 80, 9 mg/mL NaCl, adjust to pH 7 |
| 8 | 40 mg Compound (Ia)2 HCl, 250 mg Tween 80, 9 mg/mL NaCl, adjust to pH 7 |
| 9 | 5 mg Compound (Ia) 2HCl, 250 mg Kolliphor HS 15, 9 mg/mL NaCl, adjust to pH 7 |
| 10 | 10 mg Compound (Ia) 2HCl, 250 mg Kolliphor HS 15, 9 mg/mL NaCl, adjust to pH 7 |
| 11 | 15 mg Compound (Ia) 2HCl, 250 mg Kolliphor HS 15, 9 mg/mL NaCl, adjust to pH 7 |
| 12 | 20 mg Compound (Ia)2HCl, 250 mg Kolliphor HS 15, 9 mg/mL NaCl, adjust to pH 7 |
| 13 | 25 mg Compound (Ia) 2HCl, 250 mg Kolliphor HS 15, 9 mg/mL NaCl, adjust to pH 7 |
| 14 | 30 mg Compound (Ia) 2HCl, 250 mg Kolliphor HS 15, 9 mg/mL NaCl, adjust to pH 7 |
| 15 | 35 mg Compound (Ia) 2HCl, 250 mg Kolliphor HS 15, 9 mg/mL NaCl, adjust to pH 7 |
| 16 | 40 mg Compound (Ia) 2HCl, 250 mg Kolliphor HS 15, 9 mg/mL NaCl, adjust to pH 7 |
| 17 | 50 mg Compound (Ia) 2HCl, 250 mg Tween 80, 9 mg/mL NaCl, adjust to pH 7 |
| 18 | 50 mg Compound (Ia) 2HCl, 100 mg Tween 80, 9 mg/mL NaCl, adjust to pH 7 |
| 19 | 20 mg Compound (Ia) 2HCl, 100 mg Tween 80, 9 mg/mL NaCl, adjust to pH 7 |

The appearance of formulations F1 to F17 and F19 at 25° C./60% RH and 40° C./75% RH were consistent with what was observed upon initial preparation (light yellow to golden yellow solution, clear and homogeneous liquid). Precipitation was observed in F18 after 14 days at both conditions 25° C./60% RH and 40° C./75% RH. The stability results are presented in Tables 7 and 8.

TABLE 7

% Assay Results for F1 to F19

| Formulation Description | Initial (%) | After 14 days at 25° C./60% RH | After 14 days at 40° C./75% RH |
|---|---|---|---|
| F1-5 mg/mL | 95.2 | 96.8 | 96.0 |
| F2-10 mg/mL | 96.2 | 97.4 | 96.5 |
| F3-15 mg/mL | 96.6 | 96.8 | 97.2 |
| F4-20 mg/mL | 94.9 | 95.2 | 94.0 |
| F5-25 mg/mL | 97.7 | 98.2 | 99.2 |
| F6-30 mg/mL | 98.7 | 97.0 | 98.8 |
| F7-35 mg/mL | 95.6 | 94.8 | 94.8 |
| F8-40 mg/mL | 98.4 | 97.3 | 97.3 |
| F9-5 mg/mL | 98.4 | 99.5 | 99.7 |
| F10-10 mg/mL | 99.9 | 101.2 | 101.9 |
| F11-15 mg/mL | 98.2 | 100.9 | 101.8 |
| F12-20 mg/mL | 98.0 | 100.2 | 102.0 |
| F13-25 mg/mL | 99.3 | 100.9 | 102.5 |
| F14-30 mg/mL | 100.1 | 100.3 | 104.0 |
| F15-35 mg/mL | 98.5 | 100.6 | 102.4 |
| F16-40 mg/mL | 96.9 | 97.8 | 99.8 |
| F17-50 mg/mL | 87.4 | 86.7 | 87.9 |
| F19-20 mg/mL | 98.8 | 100.3 | 98.2 |

TABLE 8

% Impurity Results for F1 to F19 (% Area)

| Formulation Description | Initial (%) | | After 14 days at 25° C./60% RH (%) | | After 14 days at 40° C./75% RH (%) | |
|---|---|---|---|---|---|---|
| | Total (%) | Major (%) | Total (%) | Major (%) | Total (%) | Major (%) |
| F1-5 mg/mL | 0.96 | 0.53 | 1.72 | 0.52 | 2.25 | 0.53 |
| F2-10 mg/mL | 0.97 | 0.52 | 1.42 | 0.52 | 1.45 | 0.53 |
| F3-15 mg/mL | 0.98 | 0.52 | 1.17 | 0.52 | 1.36 | 0.53 |
| F4-20 mg/mL | 1.02 | 0.52 | 1.14 | 0.52 | 1.33 | 0.53 |
| F5-25 mg/mL | 1.06 | 0.52 | 1.23 | 0.52 | 1.32 | 0.53 |
| F6-30 mg/mL | 1.01 | 0.52 | 1.20 | 0.52 | 1.34 | 0.53 |
| F7-35 mg/mL | 1.00 | 0.52 | 1.18 | 0.52 | 1.36 | 0.53 |
| F8-40 mg/mL | 1.07 | 0.52 | 1.17 | 0.52 | 1.30 | 0.53 |
| F9-5 mg/mL | 1.09 | 0.51 | 1.08 | 0.52 | 1.40 | 0.53 |
| F10-10 mg/mL | 1.08 | 0.51 | 1.09 | 0.52 | 1.45 | 0.53 |
| F11-15 mg/mL | 1.10 | 0.51 | 1.08 | 0.52 | 1.45 | 0.53 |
| F12-20 mg/mL | 1.03 | 0.51 | 1.17 | 0.52 | 1.37 | 0.53 |
| F13-25 mg/mL | 1.07 | 0.51 | 1.18 | 0.52 | 1.39 | 0.54 |
| F14-30 mg/mL | 1.11 | 0.51 | 1.22 | 0.52 | 1.39 | 0.53 |
| F15-35 mg/mL | 1.10 | 0.51 | 1.28 | 0.52 | 1.40 | 0.54 |
| F16-40 mg/mL | 1.11 | 0.51 | 1.30 | 0.52 | 1.40 | 0.54 |
| F17-50 mg/mL | 1.10 | 0.51 | 1.28 | 0.53 | 1.41 | 0.54 |
| F19-20 mg/mL | 1.11 | 0.51 | 1.59 | 0.54 | 1.25 | 0.53 |

The results indicate a concentration range between 5 mg/mL, to 40 mg/mL of Compound (Ia) 2 HCl was stable in 250 mg Kolliphor HS 15, 9 mg NaCl per mL of water, adjusted to pH 7 (F1 to F8). It was also observed that 50 mg/mL of Compound (Ia) 2 HCl was unstable in 100 mg/mL Tween 80 (F18) and the appearance was very viscous for 50 mg/mL of Compound (Ia) 2 HCl in 250 mg/mL Tween 80 (F17). Finally it was observed that the formulation with 20 mg/mL of Compound (Ia) 2 HCl in 100 mg/mL Tween 80 (F19), showed to be quite stable, which could be one alternative for a lower concentration of Tween 80 in the formulation.

5 mg/mL and 0.2 mg/mL Compound (Ia) 2 HCl—Tween 80

Different concentrations of Tween 80 were trialled in both 5 mg/mL and 0.2 mg/mL of Compound (Ia) HCl. In addition, tests were performed with formulations of pH 4 to verify the influence of pH on the stability of the solution. The solutions were placed on stability for 14 days at 25° C./60% RH and 40° C./75% RH with the formulations detailed in Table 9.

TABLE 9

Optimal Formulations

| F# | Formulation per mL |
|---|---|
| 20 | 5 mg/mL Compound (Ia) 2HCl, 50 mg/mL Tween 80, 9 mg/mL NaCl, adjust to pH 7 |
| 21 | 5 mg/mL Compound (Ia) 2HCl, 25 mg/mL Tween 80, 9 mg/mL NaCl,, adjust to pH 7 |
| 22 | 5 mg/mL Compound (Ia) 2HCl, 10 mg/mL Tween 80, 9 mg/mL NaCl, adjust to pH 7 |
| 23 | 5 mg/mL Compound (Ia) 2HCl, 5 mg/mL Tween 80, 9 mg/mL NaCl, adjust to pH 7 |
| 24 | 0.2 mg/mL Compound (Ia) 2HCl, 20 mg/mL Tween 80, 9 mg/mL NaCl, adjust to pH 7 |
| 25 | 0.2 mg/mL Compound (Ia) 2HCl, 10 mg/mL Tween 80, 9 mg/mL NaCl, adjust to pH 7 |
| 26 | 0.2 mg/mL Compound (Ia) 2HCl, 5 mg/mL Tween 80, 9 mg/mL NaCl, adjust to pH 7 |
| 27 | 0.2 mg/mL Compound (Ia) 2HCl, 2 mg/mL Tween 80, 9 mg/mL NaCl, adjust to pH 7 |
| 28 | 0.2 mg/mL Compound (Ia) 2HCl, 9 mg/mL NaCl, adjust to pH 7 |
| 29 | 5 mg/mL Compound (Ia) 2HCl, 10 mg/mL Tween 80, 9 mg/mL NaCl, adjust to pH 4 |
| 30 | 5 mg/mL Compound (Ia) 2HCl, 5 mg/mL Tween 80, 9 mg/mL NaCl,, adjust to pH 4 |
| 31 | 0.2 mg/mL Compound (Ia) 2HCl, 1 mg/mL Tween 80, 9 mg/mL NaCl, adjust to pH 4 |

Regarding the appearance after the stability trial, formulations F20 and F21 were consistent with what was observed initially for both 25° C./60% RH and 40° C./75% RH (light yellow to yellow solution, clear and homogeneous liquid). In formulations F22 and F23, a gel was formed after the stability trial in both conditions. Formulations F24 to F27 were consistent with what was observed initially (colourless, homogeneous and clear liquid) and F28 obtained a gel and cloudy appearance for both stability conditions. Initially, after preparation, F29 showed precipitation. Crystals were formed in formulations F30 and 31 at both 25° C./60% RH and 40° C./75% RH conditions.

The solutions were submitted for HPLC analysis and the results are shown in Tables 10 and 11:

TABLE 10

% Assay Results for Formulations F20 to F27

| Formulation Description | Initial (%) | After 14 days at 25° C./60% RH (%) | After 14 days at 40° C./75% RH (%) |
|---|---|---|---|
| F20-5 mg/mL | 100.8 | 101.9 | 102.0 |
| F21-5 mg/mL | 101.0 | 101.8 | 101.3 |
| F24-0.2 mg/mL | 102.7 | 101.6 | 96.8 |
| F25-0.2 mg/mL | 104.8 | 105.1 | 103.0 |
| F26-0.2 mg/mL | 104.8 | 105.5 | 103.8 |
| F27-0.2 mg/mL | 111.9 | 113.7 | 112.9 |

TABLE 11

% Impurity Results for Formulations F20 to F27 (% Area)

| Formulation Description | Initial (%) | | After 14 days at 25° C./60% RH (%) | | After 14 days at 40° C./75% RH (%) | |
|---|---|---|---|---|---|---|
| | Total (%) | Major* (%) | Total (%) | Major* (%) | Total (%) | Major* (%) |
| F20-5 mg/mL | 1.02 | 0.50 | 1.19 | 0.52 | 1.36 | 0.53 |
| F21-5 mg/mL | 1.01 | 0.50 | 1.12 | 0.52 | 1.29 | 0.53 |
| F24-0.2 mg/mL | 1.12 | 0.49 | 1.85 | 0.52 | 6.85 | 0.53 |
| F25-0.2 mg/mL | 1.08 | 0.47 | 1.66 | 0.51 | 4.35 | 0.53 |
| F26-0.2 mg/mL | 1.02 | 0.46 | 1.30 | 0.50 | 1.82 | 0.52 |
| F27-0.2 mg/mL | 0.93 | 0.43 | 0.96 | 0.46 | 1.19 | 0.48 |

*Intermediate 3

TABLE 12

% Area of Unknown Impurity (RRT 0.821)
for Formulations F20 to F27

| Formulation Description | Initial (%) | After 14 days at 25° C./60% RH (%) | After 14 days at 40° C./75% RH (%) |
|---|---|---|---|
| F20-5 mg/mL | 0.14 | 0.21 | 0.30 |
| F21-5 mg/mL | 0.12 | 0.16 | 0.26 |
| F24-0.2 mg/mL | 0.46 | 1.15 | 6.09 |
| F25-0.2 mg/mL | 0.43 | 0.96 | 3.38 |
| F26-0.2 mg/mL | 0.38 | 0.59 | 1.05 |
| F27-0.2 mg/mL | 0.35 | 0.30 | 0.45 |

Analysing the results from 5 mg/mL of Compound (Ia) 2 HCl solutions, both demonstrated similar results as obtained in the initial tests with regard to % Assay and % Impurities.

For the concentration of 0.2 mg/mL Compound (Ia) 2HCl, Table 12 demonstrates that Formulations F24 and F25 had an unknown degradation peak (RRT 0.821). This peak could be generated due to a chemical reaction between the Tween 80 and API. In this formulation, the highest ratio of Tween 80 to Compound (Ia) 2 HCl was observed. Formulation F28, which did not contain any Tween 80, became cloudy and started to form a gel after two weeks of storage at both the 25° C./65% RH and 40° C./70% RH storage conditions. This emphases the importance of the use of a solubiliser, even at the lowest concentration of API. Formulation F27 which contained 2 mg/mL of Tween 80, was stable for two weeks at both the 25° C./65% RH and 40° C./70% RH storage conditions.

5 mg/mL and 0.2 mg/mL Compound (Ia) 2 HCl -13 Propylene Glycol and PEG 400

Formulations with propylene glycol and PEG 400 were performed. Refer to Table 13 for the formulation details.

TABLE 13

Formulations using Propylene Glycol and PEG400 as Solubilisers

| F# | Formulation per mL |
|---|---|
| 32 | 5 mg/mL Compound (Ia)2 HCl, 5% Propylene glycol, 9 mg/mL NaCl, adjust to pH 5 |
| 33 | 5 mg/mL Compound (Ia) 2HCl, 5% PEG 400, 9 mg/mL NaCl, adjust to pH 5 |
| 34 | 5 mg/mL Compound (Ia) 2HCl, 2% Propylene glycol, 9 mg/mL NaCl, |
| 35 | 5 mg/mL Compound (Ia) 2HCl, 2% PEG 400, 9 mg/mL NaCl |
| 36 | 5 mg/mL Compound (Ia) 2HCl, 0.5% Propylene glycol, 9 mg/mL NaCl |
| 37 | 5 mg/mL Compound (Ia) 2HCl, 0.5% PEG 400, 9 mg/mL NaCl |
| 38 | 5 mg/mL Compound (Ia) 2HCl, 3% Propylene glycol, 1% PEG 400, 9 mg/mL NaCl |
| 39 | 0.2 mg/mL Compound (Ia) 2HCl, 0.2% Propylene glycol, 9 mg/mL NaCl |
| 40 | 0.2 mg/mL Compound (Ia)2 HCl, 0.2% PEG 400, 9 mg/mL NaCl |
| 41 | 0.2 mg/mL Compound (Ia) 2HCl, 0.2% Propylene glycol, 0.2% PEG 400, 9 mg/mL NaCl |
| 42 | 5 mg/mL Compound (Ia) 2HCl, 2% Propylene glycol, 3% PEG 400, 9 mg/mL NaCl |
| 43 | 5 mg/mL Compound (Ia) 2HCl, 0.5% Propylene glycol, 2% PEG 400, 9 mg/mL NaCl |

Formulation F32 was prepared with and without pH adjustment to 5, no difference was observed between both solutions. Results for the appearance of formulations F32, F34 and F36 showed precipitation after 30 minutes of preparation, with a yellow shine, cloudy, heterogeneous suspension. Formulation F39 remained colourless, clear and homogeneous. Formulation F33 changed from light yellow, clear and homogeneous to light yellow heterogeneous suspension within minutes. The same is expected for formulations F35, F37, F40, F42 and F43.

5 mg/mL and 0.2 mg/mL Compound (Ia) 2 HCl —Kolliphor HS 15

Additional formulations were prepared to select the lowest concentration of Kolliphor HS 15 that could be used in order to produce a stable solution. Refer to Table 14 for formulation details.

TABLE 14

Formulations using Kolliphor HS 15 as a Solubiliser

| F# | Formulation per mL |
|---|---|
| 44 | 5 mg/mL Compound (Ia) 2HCl, 50 mg/mL Kolliphor HS 15, 9 mg/mL NaCl |
| 44 | 5 mg/mL Compound (Ia) 2HCl, 50 mg/mL Kolliphor HS 15, 9 mg/mL NaCl, adjust to pH 5 |
| 45 | 5 mg/mL Compound (Ia)2 HCl, 25 mg/mL Kolliphor HS 15, 9 mg/mL NaCl |
| 45 | 5 mg/mL Compound (Ia) 2HCl, 25 mg/mL Kolliphor HS 15, 9 mg/mL NaCl, adjust to pH 5 |
| 46 | 5 mg/mL Compound (Ia) 2HCl, 10 mg/mL Kolliphor HS 15, 9 mg/mL NaCl |
| 46 | 5 mg/mL Compound (Ia) 2HCl, 10 mg/mL Kolliphor HS 15, 9 mg/mL NaCl, adjust to pH 5 |
| 47 | 5 mg/mL Compound (Ia) 2HCl, 5 mg/mL Kolliphor HS 15, 9 mg/mL NaCl |
| 47 | 5 mg/mL Compound (Ia) 2HCl, 5 mg/mL Kolliphor HS 15, 9 mg/mL NaCl, adjust to pH 5 |
| 48 | 0.2 mg/mL Compound (Ia) 2HCl, 25 mg/mL Kolliphor HS 15, 9 mg/mL NaCl, adjust to pH 5 |
| 49 | 0.2 mg/mL Compound (Ia) 2HCl, 2 mg/mL Kolliphor HS 15, 9 mg/mL NaCl, adjust to pH 5 |

The appearance of formulations F44 and F45, with and without pH adjusted to 5, and formulation F46 without pH adjustment, were light yellow, clear and homogeneous solutions. However, formulation F46 with pH adjustment and F47 with and without pH adjustment, presented a light yellow, cloudy and heterogeneous suspension. At the lower strength, formulations F48 and F49 showed to be colourless, clear and homogeneous. So far, the lowest Kolliphor HS 15 concentration was found in formulation F45. After 1 week of stability, no difference was observed in stability of solution with and without pH adjustment.

Formulation F45=5 mg/mL Compound 2 HCl, 25 mg/mL Kolliphor HS 15 (2.5% w/w), 9 mg NaCl per mL of water.

1 mg/mL, 5 mg/mL and 15 mg/mL Compound (Ia) 2 HCl —Propylene Glycol

Further formulations using propylene glycol as a solubiliser were performed. The formulation details are listed in Table 15.

TABLE 15

Formulations using Propylene Glycol a Solubiliser

| F# | Formulation per mL |
|---|---|
| 50 | 5 mg/mL Compound (Ia) 2HCl, 100% Propylene glycol. |
| 51 | 5 mg/mL Compound (Ia) 2HCl, 80% Propylene glycol, adjust to pH 5 with NaOH. |
| 52 | 5 mg/mL Compound (Ia) 2HCl, 60% Propylene glycol, adjust to pH 5 with NaOH. |

TABLE 15-continued

Formulations using Propylene Glycol a Solubiliser

| F# | Formulation per mL |
|---|---|
| 53 | 1 mg/mL Compound (Ia) 2HCl, 80% Propylene glycol, adjust to pH 5 with NaOH. |
| 54 | 1 mg/mL Compound (Ia)2 HCl, 60% Propylene glycol, adjust to pH 5 with NaOH. |
| 55 | 15 mg/mL Compound (Ia) 2HCl, 100% Propylene glycol. |
| 56 | 15 mg/mL Compound (Ia) 2HCl, 80% Propylene glycol, adjust to pH 5 with NaOH. |
| 57 | 15 mg/mL Compound (Ia) 2HCl, 60% Propylene glycol, adjust to pH 5 with NaOH. |

Each of the formulations were sent for sterilisation via autoclave (with steam heated at 121° C. for 15 minutes), and tested for HPLC assay and related substances. The comparison between the control samples and autoclaved samples are presented in the Tables 20 and 21. In addition, the formulations were placed on stability at 5° C., 25° C./60% RH and 40° C./75% RH for 14 days. The samples autoclaved were placed on stability at 40° C./75% RH for 14 days in order to verify the stability under accelerated conditions. The stability results are shown in Tables 18, 19 and 20.

Propylene Glycol and 5% Glucose Interaction

Compound (Ia) 2 HCl solutions in Propylene Glycol were tested for possible interaction with Glucose 5% as an infusion fluid. In order to evaluate possible interaction between the solution and the infusion fluid, tests were performed using the formulations listed in Table 15. Stability of the solutions was observed for six days for appearance and pH, enough time for an eventual precipitation in the infusion bag. The mixed solution was maintained in room temperature and unprotected from light. The solubility of 5 mg/mL of Compound (Ia) 2 HCl in 100% of propylene glycol (250 mg of Compound (Ia) 2 HCl in 50 mL of propylene glycol—formulation F50) was evaluated first. The solubility was slow but was completely soluble with constant stirring for 1 hour. In order to evaluate the stability and the pH of the final solution, 18 mL of Formulation 50 was mixed with 82 mL of 5% glucose. The infusion fluid (5% Glucose) had a reading of pH 7.0 and after the addition of F50, the solution had a final pH of 2.8. After six days at room temperature and unprotected from light, the appearance of the solution was consistent with what was observed initially (colourless, homogeneous and clear liquid).

The next formulations to be tested were F51 and F52. The aim was evaluate the stability of the solution using less propylene glycol. During the preparation of these formulations, it was noted that the solubility of the API was faster than F50 and the pH was able to be adjusted to 5.0 which is close to the physiological pH.

Formulations F51 and F52 were mixed with fluid (18 mL of IV solution in 82 mL of 5% Glucose) and both solutions had the final pH of 5.7. After six days at room temperature and unprotected from light, the appearance of the solutions were consistent with what was observed initially (colourless, homogeneous and clear liquid).

Sterilization by Moist Heat

To evaluate the sterilisation by moist heat (at 121° C. for 15 minutes) and for possible degradation from this process, one sample from each formulation were reserved as a control. The HPLC tests were performed on the control sample as well as on the samples after the moist heat process. Samples were autoclaved at 121° C. for 15 minutes. Refer to Tables 16 and 17 for the % Assay results and % Area of impurities.

TABLE 16

% Assay Results for F50 to F57-Autoclave Analysis

| Formulation Description | Control (%) | After Autoclaved (%) | Absolute Difference (%) |
|---|---|---|---|
| F50-5 mg/mL-100% propylene glycol | 95.6 | 97.6 | −2.0 |
| F51-5 mg/mL-80% propylene glycol | 92.4 | 92.2 | 0.2 |
| F52-5 mg/mL-60% propylene glycol | 95.7 | 95.5 | 0.2 |
| F53-1 mg/mL-80% propylene glycol | 93.5 | 94.1 | −0.6 |
| F54-1 mg/mL-60% propylene glycol | 95.6 | 95.5 | 0.1 |
| F55-15 mg/mL-100% propylene glycol | 95.6 | 95.1 | 0.5 |
| F56-15 mg/mL-80% propylene glycol | 94.5 | 94.3 | 0.2 |
| F57-15 mg/mL-60% propylene glycol | 94.2 | 94.0 | 0.2 |

TABLE 17

% Impurity Results for F50 to F57-Autoclave analysis (% Area)

| | Control (%) | | Autoclaved (%) | |
|---|---|---|---|---|
| Formulation Description | Total (%) | Major* (%) | Total (%) | Major* (%) |
| F50-5 mg/mL | 1.58 | 1.06 | 1.59 | 1.09 |
| F51-5 mg/mL | 1.55 | 1.06 | 1.66 | 1.06 |
| F52-5 mg/mL | 1.56 | 1.06 | 1.63 | 1.07 |
| F53-1 mg/mL | 1.50 | 1.07 | 1.41 | 1.08 |
| F54-1 mg/mL | 1.54 | 1.08 | 1.39 | 1.09 |
| F55-15 mg/mL | 2.12 | 1.05 | 1.65 | 1.11 |
| F56-15 mg/mL | 1.55 | 1.08 | 1.68 | 1.07 |
| F57-15 mg/mL | 1.51 | 1.07 | 1.60 | 1.07 |

*Intermediate 3

After being autoclaved, the solutions were consistent with what was observed upon initial preparation (colourless to yellow, homogeneous and clear liquid). The potency of Compound (Ia) 2 HCl in Table 20 shows results within ±2.0% of absolute difference, which is acceptable as analytical variation. Another significant factor requiring evaluation was the HPLC results, which shows no degradation in the samples after the moist heat process, according to Table 21, the % of impurities did not increase significantly. The results show that the moist heat (autoclaving) is an appropriate method of sterilisation.

Stability Results for Formulations F50-F57

Stability results from samples described in Table 15, are listed in Tables 18 to 20.

TABLE 18

% Assay Results for F50 to F57

| Formulation Description | Initial | 5° C.* | 25° C./ 60% RH* | 40° C./ 75% RH* | Initial (A)◊ | 40° C./ 75% RH (A)◊* |
|---|---|---|---|---|---|---|
| F50-5 mg/mL | 95.6 | 96.0 | 94.9 | 96.5 | 97.6 | 96.5 |
| F51-5 mg/mL | 92.4 | 92.4 | 92.4 | 92.4 | 92.2 | 92.4 |
| F52-5 mg/mL | 95.7 | 96.1 | 96.1 | 96.3 | 95.5 | 96.3 |
| F53-1 mg/mL | 93.5 | 95.1 | 95.2 | 94.1 | 94.1 | 94.1 |
| F54-1 mg/mL | 95.6 | 95.9 | 96.2 | 96.2 | 95.5 | 96.2 |
| F55-15 mg/mL | 95.6 | 95.9 | 97.3 | 95.0 | 95.1 | 95.0 |
| F56-15 mg/mL | 94.5 | 94.4 | 94.0 | 94.3 | 94.3 | 94.3 |
| F57-15 mg/mL | 94.2 | 94.6 | 94.5 | 94.1 | 94.0 | 94.1 |

*Samples from 14 days of stability trial.
◊Sample autoclaved.

TABLE 19

% Impurity Results for F50 to F57 (% Area)

| Formulation Description | Initial (%) | | After 14 days at 5° C. (%) | | After 14 days at 25° C./60% RH (%) | | After 14 days at 40° C./75% RH (%) | |
|---|---|---|---|---|---|---|---|---|
| | Total | Major* | Total | Major* | Total | Major* | Total | Major* |
| F50-5 mg/mL | 1.58 | 1.06 | 1.58 | 1.09 | 1.60 | 1.10 | 1.61 | 1.11 |
| F51-5 mg/mL | 1.55 | 1.06 | 1.61 | 1.09 | 1.69 | 1.10 | 1.69 | 1.10 |
| F52-5 mg/mL | 1.56 | 1.06 | 1.62 | 1.10 | 1.71 | 1.09 | 1.42 | 1.10 |
| F53-1 mg/mL | 1.50 | 1.07 | 2.14 | 1.14 | 2.05 | 1.15 | 2.11 | 1.15 |
| F54-1 mg/mL | 1.54 | 1.08 | 2.12 | 1.15 | 2.03 | 1.14 | 2.06 | 1.15 |
| F55-15 mg/mL | 2.12 | 1.05 | 1.66 | 1.10 | 1.59 | 1.10 | 1.60 | 1.12 |
| F56-15 mg/mL | 1.55 | 1.08 | 1.58 | 1.10 | 1.69 | 1.55 | 1.65 | 1.10 |
| F57-15 mg/mL | 1.51 | 1.07 | 1.58 | 1.10 | 1.56 | 1.51 | 1.64 | 1.10 |

*Intermediate 3

TABLE 20

% Impurity Results for F50 to F57-Autoclave analysis (% Area)

| Formulation Description | Initial (%) | | After 14 days at 40° C./75% RH (%) | |
|---|---|---|---|---|
| | Total | Major* | Total | Major* |
| F50-5 mg/mL | 1.59 | 1.09 | 1.86 | 1.14 |
| F51-5 mg/mL | 1.66 | 1.06 | 1.70 | 1.11 |
| F52-5 mg/mL | 1.63 | 1.07 | 1.67 | 1.11 |
| F53-1 mg/mL | 1.41 | 1.08 | 2.05 | 1.16 |
| F54-1 mg/mL | 1.39 | 1.09 | 1.71 | 1.15 |
| F55-15 mg/mL | 1.65 | 1.11 | 1.85 | 1.15 |
| F56-15 mg/mL | 1.68 | 1.07 | 1.77 | 1.11 |
| F57-15 mg/mL | 1.60 | 1.07 | 1.71 | 1.11 |

*Intermediate 3

The appearance of the solutions after stability was compared with what was observed initially. After 14 days in the stability chamber for all conditions, formulations F50 to F57 remained the same with respect to appearance (colourless to yellow, clear and homogeneous solution). When the solutions that had been autoclaved were evaluated, formulations F50 to F56 remained the same with respect to appearance (colourless to yellow, clear and homogeneous solution) however, formulation F57 was observed to be yellow, cloudy and heterogeneous. Formulations F50 to F56 showed to be stable after being sterilised by moist heat at 121° C. for 15 minutes and after being placed on stability for 14 days at 5° C., 25° C./60% RH and 40° C./75% RH.

Evaluation of Osmolality

To minimise adverse effects from the solution, osmolality and pH were tested and proposed limits to meet the physiological levels. The solution osmolality was tested and the results are presented in Table 21.

The administration of the drug is an important factor to be evaluated. As the intention is to use the minimum fluid volume possible due to avoid aggravating brain swelling, infusion bags of 100 mL 5% Glucose were used as an intravenous fluid. Formulation F56 was prepared and mixed with 5% Glucose and aliquots were tested for final pH and osmolality. Analytical solutions were prepared by pipetting 2.0 mL, 3.0 mL, 4.0 mL, 5.0 mL and 6.0 mL of the Formulation F56 (representing 30, 45, 60, 75 and 90 mg of Compound (Ia)) and diluted to 100 mL with 5% glucose. Note: 6.0 mL of formulation F56 (15 mg/mL of Compound (Ia) HCl) is equivalent to 90 mg of Compound (Ia) 2 HCl. To verify the contribution of propylene glycol in the final formulation, 2.0 mL was diluted to 100 mL with 5% glucose. All samples were tested for osmolality and pH and the results are presented in Table 21.

TABLE 21

Osmolality and pH Results

| Sample Name | Osmolality (mOsm/kg) | pH |
|---|---|---|
| 5% Glucose | 294 | 6.69 |
| 2% Propylene glycol in 5% glucose | 601 | 6.36 |

TABLE 21-continued

Osmolality and pH Results

| Sample Name | Osmolality (mOsm/kg) | pH |
|---|---|---|
| 2% F56 in 5% glucose | 528 | 5.84 |
| 3% F56 in 5% glucose | 651 | 5.83 |
| 4% F56 in 5% glucose | 770 | 5.71 |
| 5% F56 in 5% glucose | 894 | 5.68 |
| 6% F56 in 5% glucose | 1023 | 5.61 |

Ideally for an infusion solution, the osmolality that should be administered should be within the range of 200 to 650 mOsm/kg. Based on the above information, another test was proposed diluting the highest doses in water for injection and in 200 mL of 5% glucose. Refer to Table 22 for a comparison of results using water for injection and 5% glucose as the infusion fluid.

TABLE 22

Osmolality Results with Different Infusion Fluid

| Sample ID | Dose | Amount of Formulation to Dilute (mL) | Infusion Diluent (final volume) | Osmolality (mOsm/kg) |
|---|---|---|---|---|
| F56_1 | 1 mg | 0.066 | 5% glucose (100 mL) | 301 |
| F56_2 | 5 mg | 0.333 | 5% glucose (100 mL) | 329 |
| F56_3 | 15 mg | 1.0 | 5% glucose (100 mL) | 401 |
| F56_4 | 30 mg | 2.0 | Water for Injection (100 mL) | 210 |
| F56_5 | 30 mg | 2.0 | 5% Glucose (200 mL) | 402 |
| F56_6 | 45 mg | 3.0 | Water for Injection (100 mL) | 317 |
| F56_7 | 45 mg | 3.0 | 5% Glucose (200 mL) | 463 |
| F56_8 | 60 mg | 4.0 | Water for Injection (100 mL) | 431 |
| F56_9 | 60 mg | 4.0 | 5% Glucose (200 mL) | 531 |
| F56_10 | 90 mg | 6.0 | Water for Injection (100 mL) | 685 |
| F56_11 | 90 mg | 6.0 | 5% Glucose (200 mL) | 640 |
| F56_12 | 90 mg | 6.0 | Water for Injection (200 mL) | 323 |

Stability of Formulation F56

Samples of formulation F56 were analysed after 3 months stability at the following conditions, 5° C., 25° C./60% RH and 40° C./75% RH. Samples were tested for appearance, pH, assay and related substances. Results are summarised in Table 23. The Formulation F56 showed to be stable after 3 months in the following conditions: 5° C., 25° C./60% RH and 40° C./75% RH.

TABLE 23

Stability Results for Formulation F56 (Time Point = 3 Months)

| | Initial | 5° C. | 25° C./ 60% RH | 40° C./ 75% RH |
|---|---|---|---|---|
| Appearance | Yellow, clear and homogenous solution. | Yellow, clear and homogenous solution. | Yellow, clear and homogenous solution. | Yellow, clear and homogenous solution. |
| pH | 5.08 | 5.07 | 5.07 | 5.04 |
| Assay (HPLC) | 100.7% | 100.7% | 100.3% | 100.5% |
| Major impurity* (% Area) | 0.53% | 0.53% | 0.54% | 0.55% |
| Total Impurities (% Area) | 1.36% | 1.32% | 1.32% | 1.37% |

*Intermediate 3

Filter Compatibility Study—Sartolab—P20—0.2 µm

As part of the manufacturing process, the solution should be filtered before sterilisation by moist heat. Therefore, a study was undertaken to verify the filter compatibility and to determine the most suitable filter to use. Assay and related substances were evaluated.

Filter tested=Sartolab—P20—Cellulose Acetate 0.2 µm (Sartorius)—tested in duplicate.

To evaluate the filter contribution, 100 mL of F56 was filtered across 10×10 mL aliquots and analysed by HPLC. A portion of the unfiltered sample was retained as a control. Refer to Tables 24 and 25 for results.

TABLE 24

Filter Compatibility-% Assay

| F56 aliquot | Assay (%)- Filter 1 | Absolute Difference*- Filter 1 | Assay (%)- Filter 2 | Absolute Difference*- Filter 2 |
|---|---|---|---|---|
| Unfiltered | 98.9 | | 98.9 | |
| F1-1 | 98.1 | −0.8 | 98.6 | −0.3 |
| F1-2 | 98.8 | −0.1 | 98.3 | −0.6 |
| F1-3 | 98.6 | −0.3 | 98.7 | −0.2 |
| F1-4 | 99.2 | 0.3 | 98.7 | −0.2 |
| F1-5 | 98.3 | −0.6 | 98.8 | −0.1 |
| F1-6 | 98.7 | −0.2 | 99.9 | 1.0 |
| F1-7 | 98.7 | −0.2 | 98.8 | −0.1 |
| F1-8 | 98.4 | −0.5 | 98.9 | 0.0 |
| F1-9 | 99.0 | 0.1 | 98.4 | −0.5 |
| F1-10 | 98.9 | 0.0 | 99.5 | 0.6 |

*Absolute Difference (%) = Assay Filtered − Assay Unfiltered

TABLE 25

Filter Compatibility-Related Substances (% Area)

| | Filter 1 | | Filter 2 | |
|---|---|---|---|---|
| F56 aliquot | Total Impurities | Major Impurity* | Total Impurities | Major Impurity* |
| Unfiltered | 1.89 | 1.08 | 1.89 | 1.08 |
| F1-1 | 1.89 | 1.08 | 1.92 | 1.08 |
| F1-2 | 1.89 | 1.08 | 1.91 | 1.08 |
| F1-3 | 1.89 | 1.08 | 1.92 | 1.07 |
| F1-4 | 1.89 | 1.08 | 1.93 | 1.08 |
| F1-5 | 1.91 | 1.08 | 1.92 | 1.08 |
| F1-6 | 1.91 | 1.08 | 1.92 | 1.08 |
| F1-7 | 1.90 | 1.08 | 1.92 | 1.08 |
| F1-8 | 1.91 | 1.08 | 1.90 | 1.07 |
| F1-9 | 1.92 | 1.08 | 1.90 | 1.08 |
| F1-10 | 1.92 | 1.08 | 1.91 | 1.08 |

*Intermediate 3

The potency of Compound (Ia) 2 HCl in Table 25 shows results within ±2.0% of absolute difference, which is acceptable as analytical variation. No interference was observed in Potency (Assay %) or Related Substances (% Area) after 100 mL of solution was filtered. The filter Sartolab—P20—Cellulose Acetate 0.2 µm was considered suitable for use in the manufacturing process.

GLP Manufacture

Formulation F56 was manufactured at scale, filled into vials and further sterilisation by moist heat. Analytical results to support production were performed and are listed in Tables 26.

TABLE 26

15 mg/mL Compound (Ia) 2HCl Injectable solution

| Test | Bulk Solution | Finish Product |
|---|---|---|
| Appearance | Colourless, clear and homogenous solution. | Colourless, clear and homogenous solution. |
| pH | 4.82 | 4.80 |
| Assay (HPLC) | 100.2% | 98.8% |
| Major impurity* (% Area) | N.A. | 0.71% |
| Total Impurities (% Area) | N.A. | 1.70% |
| Uniformity of Dosage | N.A. | Ave: 99.2% RSD: 1.5% |
| Osmolality | N.A. | 476 mOsm/kg |

*Intermediate 3

Filter Compatibility—Sartopure—PP2—8 µm

A filter with a larger pore size (to assist with processing the solution at scale in production at a faster rate) was tested and the potency (Assay %) was evaluated.

Filter tested=Sartopure—PP2—0.8 µm, (Sartorius—Lot #609011603) tested in duplicate.

To evaluate the filter contribution, 100 mL of F56 was filtered across 10×10 mL aliquots and analysed by HPLC. A portion of unfiltered sample was retained as a control, Refer to Table 27 for results.

TABLE 27

Filter Compatibility-% Assay

| F56 aliquot | Assay (%)- Filter 1 | Absolute Difference*- Filter 1 | Assay (%)- Filter 2 | Absolute Difference*- Filter 2 |
|---|---|---|---|---|
| Unfiltered | 96.4 | | 96.4 | |
| F1-1 | 95.9 | −0.5 | 97.0 | 0.6 |
| F1-2 | 96.7 | 0.3 | 97.1 | 0.7 |
| F1-3 | 97.3 | 0.9 | 97.0 | 0.6 |
| F1-4 | 96.0 | −0.4 | 96.4 | 0.0 |
| F1-5 | 96.9 | 0.4 | 96.6 | 0.2 |
| F1-6 | 96.7 | 0.3 | 96.9 | 0.4 |
| F1-7 | 96.9 | 0.4 | 97.1 | 0.7 |
| F1-8 | 96.7 | 0.3 | 97.0 | 0.6 |
| F1-9 | 96.6 | 0.2 | 97.5 | 1.1 |
| F1-10 | 96.4 | 0.0 | 97.8 | 1.4 |

*Absolute Difference (%) = Assay Filtered − Assay Unfiltered

The potency of Compound (Ia) 2 HCl in Table 27 shows results within ±2.0% of absolute difference, which is acceptable as analytical variation. No interference was observed in Potency (Assay %) after 100 mL of solution was filtered. The filter Sartopure—PP2—0.8 µm was considered suitable for use in the manufacture.

Infusion Study

This study was performed in order to determine the stability and compatibility of Compound (Ia) 2 HCl 15 mg/mL intravenous injection formulation in 200 mL 5% glucose infusion bags and the infusion lines intended for use in the Phase I Clinical Trial. In this study, Compound (Ia) 2 HCl 15 mg/mL intravenous injection was mixed in 5% glucose infusion bags to provide concentrations of 0.05 mg/mL and 0.45 mg/mL.

Infusion bags containing a theoretical volume of 250 mL of 5% glucose were used to prepare 200 mL 5% glucose bags. A 50 mL syringe and 18G needle was used to remove 200 mL of 5% glucose from 250 mL 5% Glucose Viaflex Infusion Bags and added to 500 mL Empty Viaflex Infusion Bags. The appropriate amount of Compound (Ia) HCl was accurately weighed in a syringe and injected into the infusion bags containing 200 mL of 5% glucose.

The dosed bags were stored at 5° C.±3° C. protected from light, 25° C./60% RH protected from light and ambient room temperature, unprotected from light exposed to 'normal room light'. The infusion bags were tested at initial, 4, 8 and 24 hours. The infusion lines were tested using the ambient room temperature bags after the 24 hour timepoint.

Testing of the dosed bags was performed by connecting infusion lines to the infusion bags and draining some solution through the infusion line. Cannula were connected to the infusion lines and samples were collected to perform assay testings.

The results showed that Compound (Ia) 2 HCl 15 mg/mL intravenous injection is stable for parameters of appearance of solution, pH, assay and related substances when mixed with 200 mL 5% glucose for all conditions listed above for a maximum 8 hours.

The invention claime is:

1. A reconstitutable, parenteral, pharmaceutical composition comprising:
  (i) a compound of Formula (I) or a pharmaceutically acceptable salt, solvate or prodrug thereof:

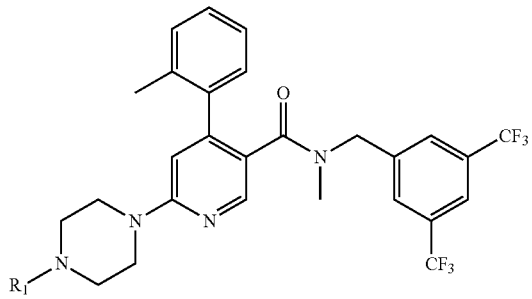

Formula (I)

wherein R1 is H or C1-4 alkyl; and ii) at least one solubiliser selected from the group comprising of a glycerol, glycerin, dimethylacetamide, N-methyl-2-pyrrolidone, propylene glycol, polyethylene glycol based solubilizers, ricinoleate based solubiliser, cyclodextrin, polyethoxylated caster oil based solubilizers, solubilizers derived from polyethoxylated sorbitan and oleic acid, castor oil, cottonseed oil, triglyceride, sesame oil, soybean oil, or safflower oil, wherein the at least one solubiliser is present in the composition in an amount of about 10% to about 99.8% wt/wt based on the total weight of the composition, and wherein the composition is intended to be reconstituted in an amount of about 5% glucose solution as an infusion fluid to achieve an osmolality of 528 mOsm/kg to 1023 mOsm/kg.

2. The reconstitutable, parenteral, pharmaceutical composition according to claim 1, wherein the compound of Formula (I) is present in the composition in an amount of about 0.2% to about 1.8% wt/wt based on the total weight of the composition.

3. The reconstitutable, parenteral, pharmaceutical composition according to claim 1, wherein the wt/wt ratio of compound of Formula (I) or a pharmaceutically acceptable salt, solvate or prodrug thereof to solubiliser is about 1:40 to about 1:250.

4. The reconstitutable, parenteral, pharmaceutical composition according to claim 1, wherein the composition is in the form of a concentrate, solution, dispersion, solid, or powder.

5. The reconstitutable, parenteral, pharmaceutical composition according to claim 1, wherein $R_1$ is selected from H, methyl, ethyl, n-propyl or iso-propyl.

6. The reconstitutable, parenteral, pharmaceutical composition according to claim 1, wherein the composition is a reconstitutable, intravenous, pharmaceutical composition.

7. The reconstitutable, intravenous, pharmaceutical composition according to claim 6, wherein the at least one solubiliser selected from the group comprising of a glycerol, glycerin, dimethylacetamide, N-methyl-2-pyrrolidone, propylene glycol, polyethylene glycol based solubilizers, ricinoleate based solubiliser, cyclodextrin, polyethoxylated caster oil based solubilizers, or solubilizers derived from polyethoxylated sorbitan and oleic acid.

8. The composition according to claim 1, wherein the compound of Formula (I) is:

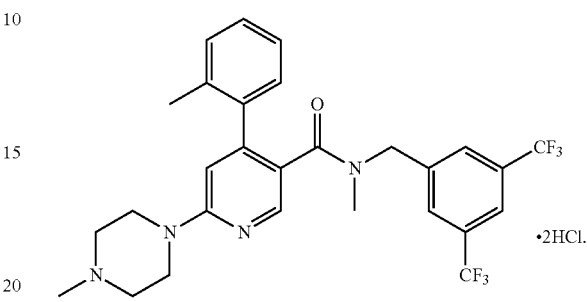

* * * * *